US012569516B2

(12) United States Patent (10) Patent No.: US 12,569,516 B2
Gu et al. (45) **Date of Patent: \*Mar. 10, 2026**

(54) SUBJECT-SPECIFIC TUMOR INHIBITING CELLS AND THE USE THEREOF

(71) Applicants: EZY BIOTECH LLC, Wilmington, DE (US); ADAERATA, LIMITED PARTNERSHIP, Montréal (CA)

(72) Inventors: Hua Gu, Westmount (CA); Gang G Xu, Wilmington, DE (US); Adeline Gadzinski, Colomb (CA); Haijun Tong, Shanghai (CN)

( * ) Notice: Subject to any disclaimer, the term of this patent is extended or adjusted under 35 U.S.C. 154(b) by 242 days.

This patent is subject to a terminal disclaimer.

(21) Appl. No.: 18/451,125

(22) Filed: Aug. 17, 2023

(65) Prior Publication Data

US 2024/0269177 A1 Aug. 15, 2024

Related U.S. Application Data

(62) Division of application No. 16/762,934, filed as application No. PCT/US2018/065578 on Dec. 14, 2018, now Pat. No. 11,766,455.

(60) Provisional application No. 62/598,986, filed on Dec. 14, 2017.

(51) Int. Cl.
| | |
|---|---|
| *A61K 35/17* | (2025.01) |
| *A61K 45/06* | (2006.01) |
| *A61P 35/00* | (2006.01) |
| *C12N 5/0783* | (2010.01) |
| *C12N 9/22* | (2006.01) |
| *C12N 15/11* | (2006.01) |

(52) U.S. Cl.
CPC .............. *A61K 35/17* (2013.01); *A61K 45/06* (2013.01); *A61P 35/00* (2018.01); *C12N 5/0636* (2013.01); *C12N 9/22* (2013.01); *C12N 15/11* (2013.01); *C12N 2310/20* (2017.05)

(58) Field of Classification Search
CPC .............................. A61K 35/17; C12N 5/0646
See application file for complete search history.

(56) References Cited

U.S. PATENT DOCUMENTS

| | | | | |
|---|---|---|---|---|
| 11,766,455 B2 * | 9/2023 | Gu | ......................... | A61K 45/06 |
| | | | | 424/85.2 |
| 2011/0287056 A1 * | 11/2011 | Gu | ......................... | A61P 37/04 |
| | | | | 435/7.1 |

* cited by examiner

*Primary Examiner* — Brian Gangle
*Assistant Examiner* — Lakia J Jackson-Tongue
(74) *Attorney, Agent, or Firm* — Gann G. Xu

(57) ABSTRACT

This disclosure is directed to a pharmaceutical composition comprises tumor inhibiting cells (TICs) and a method for producing the TICs. The tumor inhibiting cells can be derived from immune cells including T cells, NK cells, or a combination thereof, modified to have inactivated Cbl-b gene alleles and free from Cbl-b bio-function (Cbl-b$^{-/-}$ TICs). The Cbl-b$^{-/-}$ TICs are free from deoxyribonucleic acids exogenous to the immune cells. The immune cells can be isolated using a portable cell isolation and modification device. This disclosure is further directed to a method for treating tumorous conditions in subjects. The pharmaceutical composition can provide a subject-specific tumor treatment.

5 Claims, 7 Drawing Sheets
Specification includes a Sequence Listing.

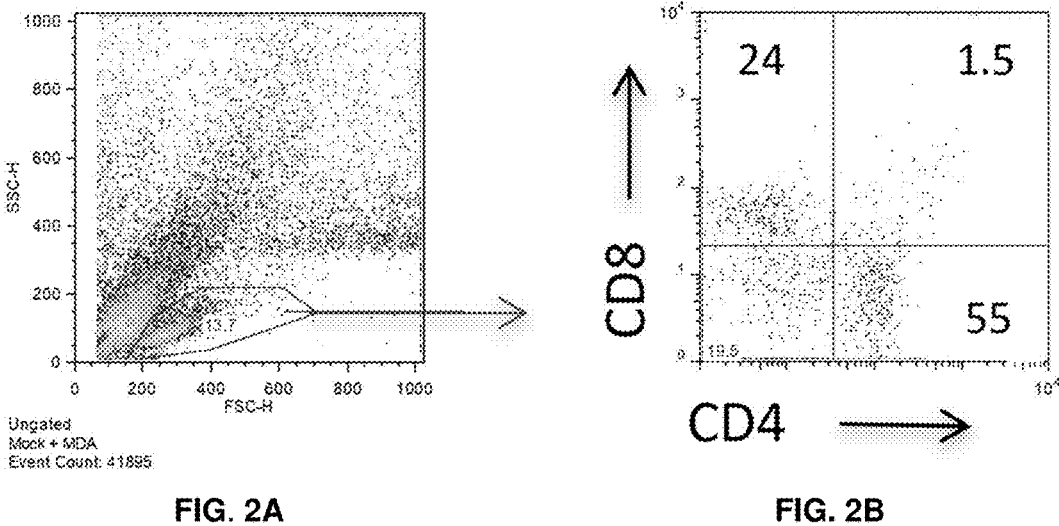
FIG. 2A                                    FIG. 2B
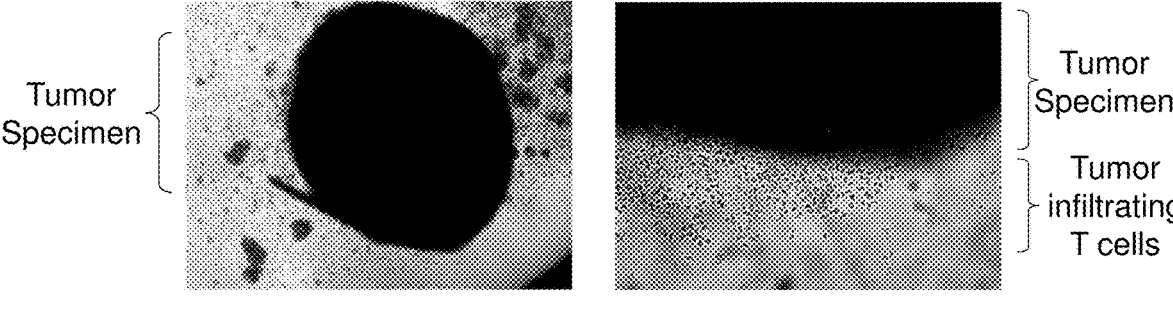
FIG. 2C                                    FIG. 2D

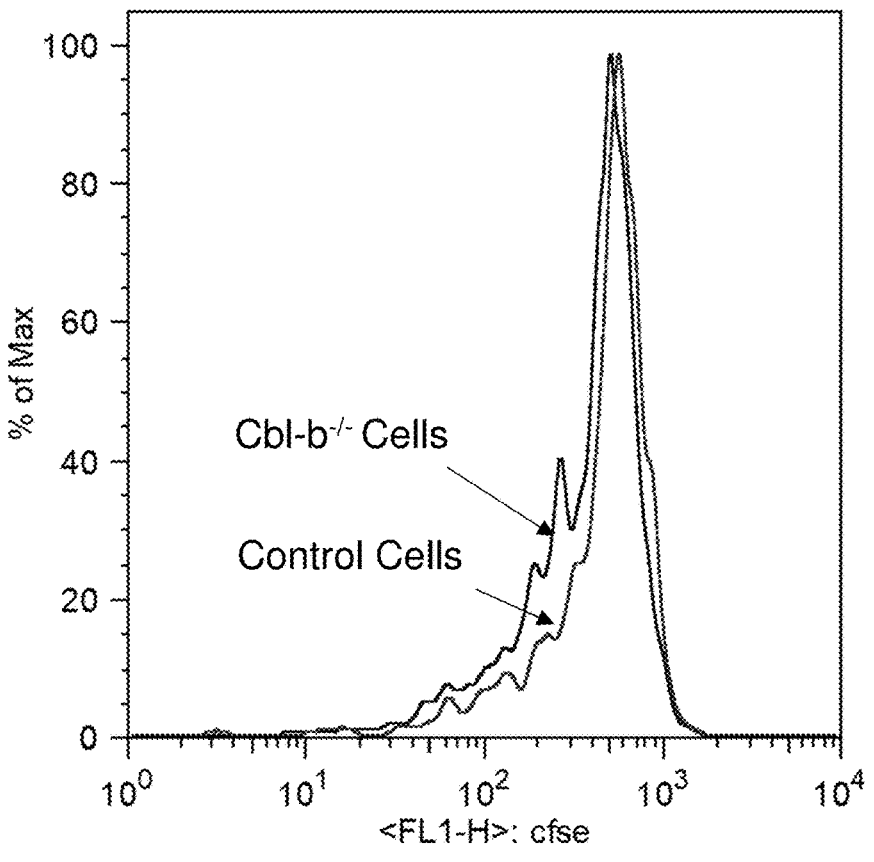
FIG. 6
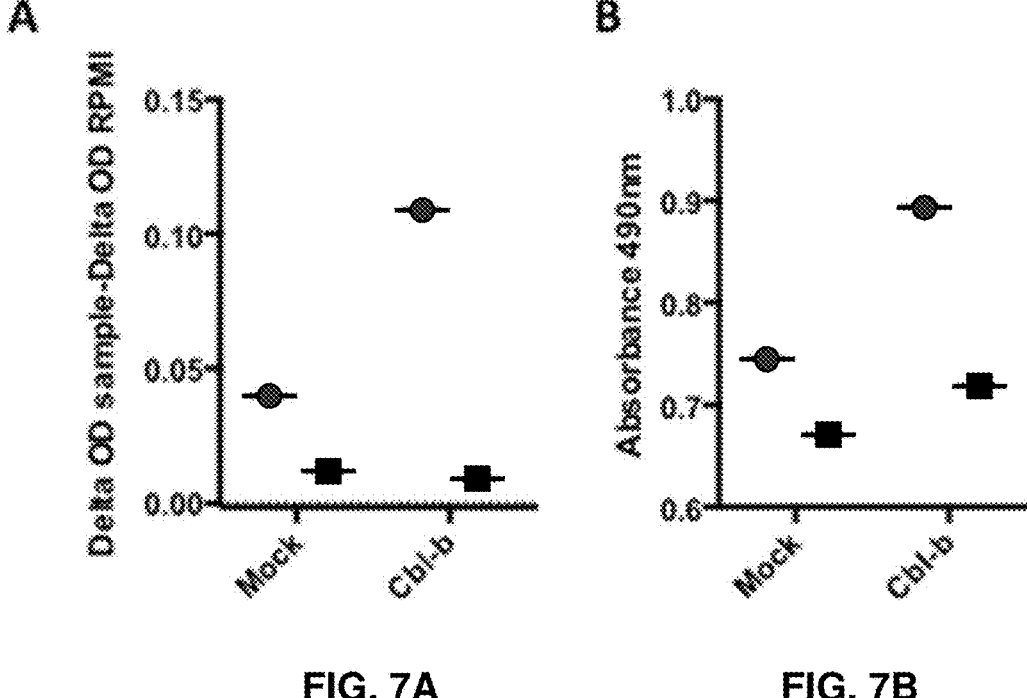
FIG. 7A                              FIG. 7B

SUBJECT-SPECIFIC TUMOR INHIBITING CELLS AND THE USE THEREOF

CROSS REFERENCE TO RELATED APPLICATION

This is a divisional application of U.S. application Ser. No. 16/762,934, filed on May 10, 2020, now allowed, which is a National Stage International Application of PCT/US2018/065578, filed on Dec. 14, 2018, which claims the benefit of U.S. Provisional Application Ser. No. 62/598,926, filed on Dec. 14, 2017, the disclosure of which is incorporated by reference herein for all purposes as if fully set forth.

FIELD OF THE INVENTION

This disclosure is directed to a pharmaceutical composition comprising subject-specific tumor inhibiting cells (TICs) and the use for treating a tumor or tumors in a subject. This disclosure is further directed to a method for producing subject-specific tumor inhibiting cells (TICs) by modifying one or more genes of immune cells.

BACKGROUND OF THE INVENTION

Immunotherapy is a therapeutical method to treat tumors that utilizes host immune system's natural capability to specifically target and destroy tumor cells. However, tumor cells can sometimes escape detection and destructions by host immune systems. Tumor cells can have multiple mechanisms to escape host immune systems, such as expressing inhibitory molecules on the tumor cell surface that can inactivate host immune cells or making it more difficult for the host immune system to detect tumor cells. Tumor cells can also produce factors or to induce surrounding cells to release substances that suppress host immune responses and stimulate tumor cell proliferation. For example, TGF-β produced by tumor cells or surrounding cells is one of the mechanisms that can inhibit T cell proliferation and becoming cytotoxic to tumor cells.

Different immunotherapy approaches have been developed to overcome immune escaping mechanisms of tumor cells and to increase the efficacy of the immune system to eradicate tumor cells.

One approach is immune cell therapy, also known as adoptive cell therapy (ACT), in that, immune cells such as T cells or natural killer cells (NK cells) purified from a patient are expanded and modified in vitro. Subsequently, these modified immune cells are transferred into the same patient for treating a disease such as a cancer. Limited success has been reported, such as those described in U.S. Pat. Nos. 7,446,190; 8,399,645; 8,637,307; 9,161,971 and 9,328,156 relating to T cells; and U.S. Pat. Nos. 8,026,097 and 8,313,943 relating to NK cells. Unfortunately, immune cells transferred back to the patient have to face a hostile tumor environment, which may disable their tumor killing or inhibiting potency, thus preventing them from inducing tumor regression.

Another approach, named Chimeric Antigen Receptor (CAR)-T cell therapy (CAR-T), consists of a T cell therapy in which T cells are equipped with a recombinant T cell antigen receptor (TCR) containing an extracellular antibody domain that recognizes a tumor antigen fused to an intracellular costimulatory signaling module that can simultaneously provide TCR and costimulatory signals. So far, this approach has shown some successes in treating B cell lymphomas and recently received US Federal Food and Drug Administration (US FDA) approval for the treatment of patients with relapsed and refractory diffuse large B cell lymphoma and B cell acute lymphoblastic leukemia in pediatric and young adult patients. However, the similar CAR-T strategy is difficult to apply to solid tumors because CAR-T receptors must recognize a cell surface protein antigen that is only expressed by tumor but not by normal cells, a condition that is hard to meet in most tumors. Furthermore, CAR-T's chimeric TCR recognizes a single epitope expressed by tumor cells; thus, the treatment can become completely useless if tumor cells lose this particular epitope as the disease progresses. In this regard, there is an urgent need to develop new strategies that can not only overcome the aforementioned immune escaping mechanisms but also be applied to a wide range of tumors.

Yet another approach is to use therapeutic antibodies, also known as antibody-drug conjugates (ADCs), in which, a biologically active cytotoxic substance is chemically conjugated to a tumor recognizing antibody or a fragment of an antibody providing targeted cytotoxicity to tumor cells. Some antibodies can even destroy tumor cells without the conjugated cytotoxic substance. A number of ADCs have been approved by FDA for treating breast cancer, Hodgkin's lymphoma, and certain types of T cell lymphomas. Some examples of ADCs are described in U.S. Pat. Nos. 8,337, 856; 7,829,531 and 5,736,137.

Chemical inhibitors that can block or limit immune responses can also be used in immunotherapy. Examples can include inhibitors known as checkpoint inhibitors that can block the activity of immune checkpoint proteins, such as CTLA4 and PD-1. A number of immune checkpoint inhibitor drugs have been approved by FDA to treat several types of cancers including melanoma and non-small cell lung cancer. However, immune checkpoint inhibitors are often only effective in some patients and in limited types of cancers. In addition, they may evoke unwanted immune responses that lead to autoimmune disorders due to their indiscriminate targets. Some examples of immune checkpoint inhibitors are described in U.S. Pat. Nos. 7,741,345; 8,846,681 and 8,722,019.

Cancer vaccine is yet another therapeutic approach that boosts the host immune system in patients to induce tumor regression. Limited success has been reported for treating certain metastatic prostate cancer. One example is described in U.S. Pat. No. 8,153,120.

Proteins that regulate immune system activity can also be used in immunotherapy. These proteins can include cytokines, such as interleukins and interferons, and certain growth factors. These proteins may help to stimulate immune cells and may be combined with immune cell therapy.

Each of the aforementioned approaches has limitations: some are only effective in certain patients and in limited types of cancer, some have transient effect, some introduce bacteria, virus or retrovirus DNA or RNA into the host immune cells and some may evoke indiscriminate interferences with normal immune tolerance. Therefore, there are clear clinic needs for new and improved methods and compositions for treating tumors.

SUMMARY OF INVENTION

This disclosure is directed to a pharmaceutical composition comprising a population of tumor inhibiting cells (TICs) that can include Cbl-b$^{-/-}$ tumor inhibiting cells (Cbl-b$^{-/-}$ TICs) modified from tumor-specific immune cells, wherein the Cbl-b$^{-/-}$ TICs have inactivated Cbl-b genomic alleles and are free from Cbl-b bio-function, and wherein the Cbl-b$^{-/-}$ TICS are free from deoxyribonucleic acids exogenous to the immune cells and free from viral nucleic acids.

This disclosure is further directed to a method for producing Cbl-b$^{-/-}$ tumor inhibiting cells (Cbl-b$^{-/-}$ TICs), the method comprising the steps of inactivating genomic Cbl-b genes of immune cells to produce the Cbl-b$^{-/-}$ TICs, wherein the Cbl-b$^{-/-}$ TICs are free from Cbl-b bio-function and free from deoxyribonucleic acids exogenous to the immune cells and free from viral nucleic acids.

This disclosure is further directed to a method for treating a tumorous condition of a subject in need thereof, the method comprising the steps of:

a) inactivating genomic Cbl-b genes of tumor-specific immune cells of the subject to produce Cbl-b$^{-/-}$ tumor inhibiting cells (Cbl-b$^{-/-}$ TICs), wherein the Cbl-b$^{-/-}$ TICs have inactivated Cbl-b gene alleles and are free from Cbl-b bio-function, and wherein the Cbl-b$^{-/-}$ TICs are free from deoxyribonucleic acids exogenous to the immune cells and free from viral nucleic acids;

b) optionally, propagating the Cbl-b$^{-/-}$ TICs in in vitro cell culture; and c) administering the Cbl-b$^{-/-}$ TICs to the subject.

This disclosure is further directed to a method for producing Cbl-b$^{-/-}$ tumor inhibiting cells (Cbl-b$^{-/-}$ TICs) comprising the step of inactivating genomic Cbl-b genes of immune cells to produce the Cbl-b$^{-/-}$ TICs, wherein the Cbl-b$^{-/-}$ TICs are free from Cbl-b bio-function and free from deoxyribonucleic acids exogenous to the immune cells and free from viral nucleic acids exogenous to the immune cells.

This disclosure is further directed to a method for producing Cbl-b$^{-/-}$ TICs using a xenograft tumor.

This disclosure is further directed to tumor inhibiting cells (TICs) produced by inactivating one or more of the target genes selected from Cbl-b, CTLA4, PD-1, LAG3, TIM3, CD73, KIR (killer inhibitory receptor), Fas, AHR (aryl hydrocarbon receptor), Smad2, Smad4, TGFBR (TGF-beta receptor), ILT-3, or a combination thereof.

BRIEF DESCRIPTION OF THE FIGURES

FIG. 2A-FIG. 2D. Isolation and Expansion of TILs from Fresh Human Breast Cancer Specimen. (A) Flow cytometric analysis of total tumor infiltrating cells (TILs) isolated from in vitro cultured breast cancer specimens with T cells indicated with the lined gate and (B) The T cells gated in (A) are stained with anti-CD4 and anti-CD8 antibodies and sorted with FACS showing CD4$^+$ and CD8$^+$ T cells with percentages shown. (C) DIC (Differential Interference Contrast) microscopic view of one piece of breast cancer specimen grew in a 48-well tissue culture plate. (D) High magnification DIC view of breast cancer TILs in the culture.

FIG. 6. Examples of isolated tumor responding cells. TILs were isolated from human breast cancer specimens. Cells were either mock transfected (Control Cells) or transfected with Cas9-sgRNA$^{Cbl-b}$ (Cbl-b$^{-/-}$ Cells), labeled with CFSE and stimulated with MDA-MB-231 tumor cells. Proliferating cells (CFSE$^{lo}$) and non-proliferating cells (CFSE$^{hi}$) were subjected for purification by FACS based on the CFSE intensity. Human Cbl-b$^{-/-}$ TILs (Cbl-b/Cells) exhibited more cell divisions compared to their mock-transfected counterparts (Control).

FIG. 7A-FIG. 7B. Anti-tumor activity assay showing T cells against a human tumor cell line. Tumor responding (CFSE$^{lo}$) and non-responding (CFSE$^{hi}$) cells were cocultured with MDA-MB-231 tumor cells for 24 hours. Cytokine secretion and tumor cell killing activity were determined by ELISA and LDH release assays, respectively. (A): ELISA measurement of INF-γ production in the supernatant of the T cell culture after co-cultured with MDA-MB-231 tumor cells. (B): Tumor cell death measured by the LDH release assay. LDH release is proportional to cell death. Solid circle: CFSE TIL cells, tumor responders from Mock or Cas9-sgRNA$^{Cbl-b}$ transfected cells; Solid square: CFSE$^{hi}$ cells, non-responders TILs to MDA-MB-231 tumor cells.

DETAILED DESCRIPTION OF THE INVENTION

Figure 1:
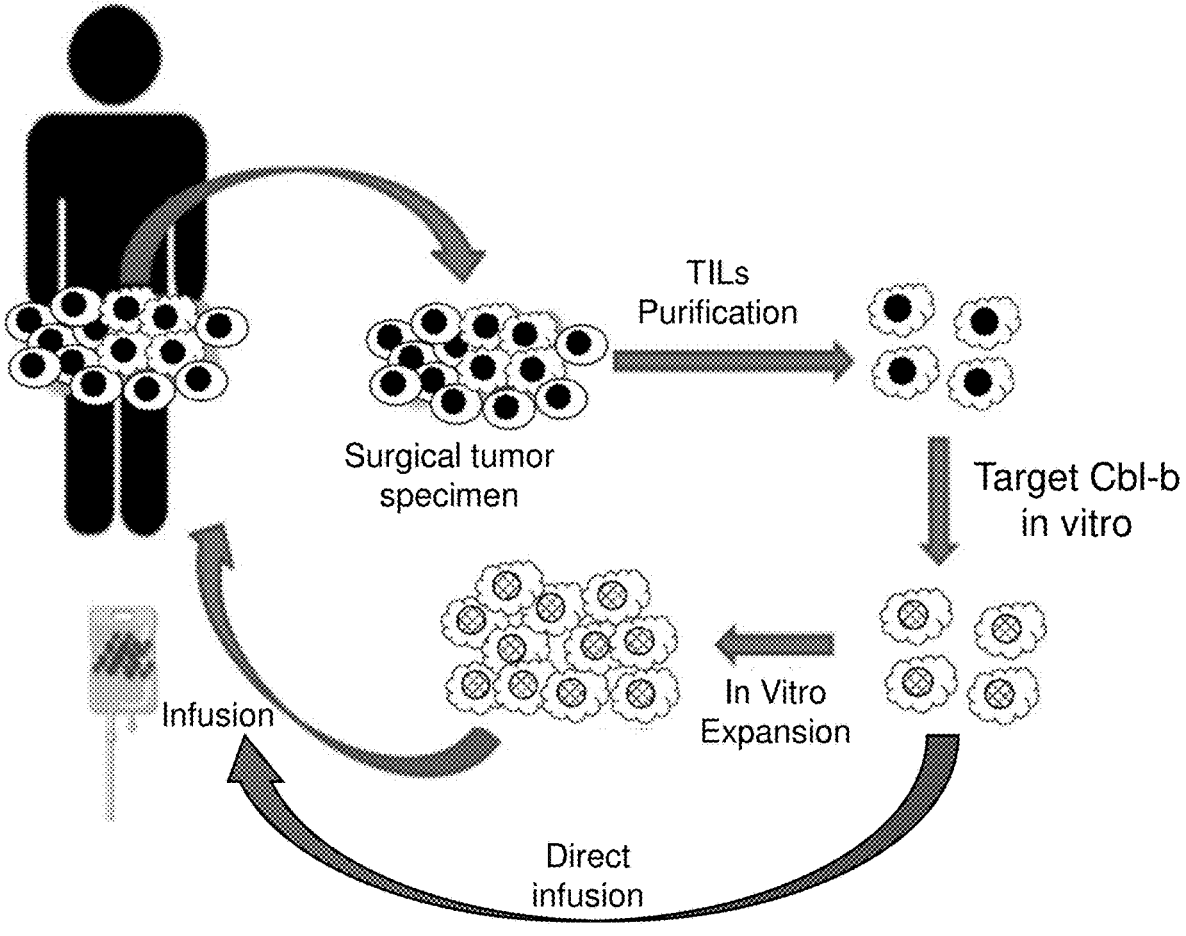
FIG. 1. Schematic diagram of an example of a process and the use of modified cells to treat a subject. A tumor specimen is surgically removed from the subject, TILs are purified and modified to inactivate the Cbl-b genes in vitro, which are then expanded in vitro and subsequently infused into the subject.

The features and advantages of the present invention will be more readily understood, by those of ordinary skill in the art, from reading the following detailed description. It is to be appreciated that certain features of the invention, which are, for clarity, described above and below in the context of separate embodiments, may also be provided in combination in a single embodiment. Conversely, various features of the invention that are, for brevity, described in the context of a single embodiment, may also be provided separately or in any sub-combination. In addition, references in the singular may also include the plural (for example, "a" and "an" may refer to one, or one or more) unless the context specifically states otherwise.

The use of numerical values in the various ranges specified in this application, unless expressly indicated otherwise, are stated as approximations as though the minimum and maximum values within the stated ranges were both proceeded by the word "about." In this manner, slight variations above and below the stated ranges can be used to achieve substantially the same results as values within the ranges. Also, the disclosure of these ranges is intended as a continuous range including every value between the minimum and maximum values.

This disclosure is directed to a pharmaceutical composition that comprises a population of Cbl-b/tumor inhibiting cells (Cbl-b$^{-/-}$ TICs) modified from immune cells, wherein the Cbl-b$^{-/-}$ TICs have inactivated Cbl-b genomic alleles and are free from Cbl-b bio-function, and wherein the Cbl-b$^{-/-}$ TICs are free from deoxyribonucleic acids (DNA) exogenous to the immune cells and free from viral nucleic acids exogenous to the immune cells including virus DNA and virus RNA (ribonucleic acids).

The Cbl-b/tumor inhibiting cells (Cbl-b$^{-/-}$ TICs) of this invention can be modified from tumor-specific immune cells, wherein the Cbl-b$^{-/-}$ TICs can inhibit one or more specific tumor or tumors.

The term "Cbl-b$^{-/-}$" refers to genotype of a cell wherein all Cbl-b gene alleles of the cell are inactivated, that means, for a diploid cell, both gene alleles are inactive and for a cell has more than two Cbl-b alleles, all of those gene alleles are inactivated. As used herein throughout this disclosure, a Cbl-b$^{-/-}$ cell is free from the Cbl-b bio-function.

The terms "tumor" and "cancer" are used interchangeably in this disclosure unless specified otherwise and refers to abnormal mass or growth of tissue or cells including solid tumors and non-solid tumors. A tumor can be benign or malignant. Different types of solid tumors are typically named based on the type of cells that form them. Examples of solid tumors can include sarcomas, carcinomas, lymphomas and other solid tumors disclosed herein or known to those in the medical field. Leukemia, also commonly referred to as a cancer or malignancy of blood cells, is an example of a non-solid tumor. Malignant tumors are cells with uncontrolled growths that can invade surrounding tissues, metastasize (spread to other organs) and may eventually cause lethality if untreated. The term "tumor" can also include neoplasm, an abnormal growth of cells that can grow faster or die less than normal cells. Neoplasms can impact and damage adjacent tissues, cells or organ structures. Neoplasm can include benign (usually curable) or malignant (cancerous) growths. The term "tumor" in this disclosure can also include a benign tumor that is non-malignant or non-cancerous. A benign tumor is usually localized, and does not spread to other parts of the body, although some benign tumors can become very large that cause stress or have other negative impact on surrounding tissues or organ structures. The term "tumor" can include both malignant tumor and malignant neoplasm that are of cancerous growths. The tumor can include vascularized, non-vascularized or not yet substantially vascularized tumors. The term "tumorous condition" refers to a tumor as mentioned herein or a condition of a subject that a tumor can potentially develop or progress. For example, a patient can be in a tumorous condition if multiple cancer indicators or some cancerous cells are detected even without any detectable tumor.

The term "tumor inhibiting cells" or "TICs" refers to cells that can inhibit the growth of tumor cells, induce tumor regression or destroy tumor cells. The tumor inhibiting cells can include both natural and modified immune cells, such as T cells (thymus cells), B cells (bone marrow- or bursa-derived cells) and NK cells (natural killer cells) that are the major cellular components of innate and adaptive immune responses. In one example, tumor inhibiting cells can include natural or modified T cells and NK cells that have potent cytotoxicity to tumor cells leading inhibition of tumor growth or destruction of a tumor. In another example, tumor inhibiting cells can include CD8$^+$-cytotoxic T lymphocytes (CTLs). In yet another example, tumor inhibiting cells can include B-cells that produce antibodies against tumor cells. Modified immune cells can be modified with chemical or biological reagents, such as chemical inhibitors, activators, antibodies, vaccines, a different set of cells, or a combination thereof. Modified immune cells can be modified with genetic materials such as gene expression vehicles that can produce one or more desired proteins or nuclei acids in immune cells that can impact cell functions. Examples can include the aforementioned modified T cells and NK cells. Modified immune cells can be modified with genetic materials that alter one or more of gene alleles of immune cells. In a preferred embodiment, modified immune cells can be Cbl-b$^{-/-}$ tumor inhibiting cells (herein referred to as Cbl-b$^{-/-}$ TICs) modified from immune cells, wherein the Cbl-b$^{-/-}$ TICs have inactivated Cbl-b genomic alleles and are free from Cbl-b bio-function. In a further embodiment, modified immune cells (Cbl-b$^{-/-}$ TICs) can comprise Cbl-b$^{-/-}$ CD8$^+$ T cells, Cbl-b$^{-/-}$ NK cells, or a combination thereof.

The Cbl-b gene encodes a Cbl-b protein that is a member of the Cbl protein family, which is a RING-finger domain-containing E3 ubiquitin ligase involved in various signaling pathways. Gu et al. reported that the loss or reduction of the Cbl-b gene function in T cells can render T cells resistant to TGF-β suppression and enhance T cell responses to weak tumor antigens in the absence of CD28 co-stimulation, consequently eradicating tumors in animal models as described in U.S. Pat. No. 9,334,522, herein incorporated by reference.

The Cbl-b$^{-/-}$ TICs of this invention are free from deoxyribonucleic acids (DNA) exogenous to the immune cells and free from viral nucleic acids exogenous to the immune cells. The pharmaceutical composition can also be free from nucleic acids exogenous to the unmodified T cells and free from viral nucleic acids including viral DNA and viral RNA. As described herein, the Cbl-b$^{-/-}$ TICs can be produced by introducing into immune cells a genomic modification component that is free from deoxyribonucleic acids (DNA) exogenous to the immune cells and free from viral nucleic acids exogenous to the immune cells including virus DNA and virus RNA. The term "exogenous to the immune cells" refers to exogenous DNA that are added to the immune cells, originated outside the host of the immune cells or existing transiently in the immune cells including natural DNAs isolated or modified from organisms other than the host of the immune cells or synthesized DNAs. The exogenous DNA can include expression vectors; fragments of expression vectors; cloning vectors; fragments of cloning vectors; fragments of functional or non-functional DNAs such as promoters, enhancers, operons, coding regions, non-coding regions, replication origins and any other DNAs that are originated from bacteria, phages, viruses or any organisms other the host of the immune cells. Throughout this disclosure, any DNA, RNA, virus DNA, virus RNA, other genetic materials, or a combination thereof that have already become part of the stable genetic content of the immune cells prior to the modification or prior to the isolation of the immune cells are considered endogenous to the immune cells, the TICs or the subject, respectively.

The Cbl-b$^{-/-}$ TICs can be autologous. The Cbl-b$^{-/-}$ TICs can also be histological compatible to a subject, such as a human subject or a tumor patient, meaning that the Cbl-b$^{-/-}$ TICs are not rejected by the subject's immune response nor acting against normal cells or tissues of the subject. The immune cells can be from the same subject (the tumor patient, i.e., autologous). The immune cells can also be from the subject before the tumor occurs (pre-tumor patient). The immune cells can also be from a donor subject that has the major histocompatibility complex (MHC) and other immune response components compatible to the subject. In one embodiment, the immune cells are from the subject. In another embodiment, the immune cells are from a donor subject wherein the immune cells are MHC compatible to the subject. In a further embodiment, the immune cells are from the subject that has already developed a tumor.

The term "subject" used herein can include an animal with or without a tumor, a healthy human without a tumor, a human patient with a tumor or a metastatic tumor, a human patient who has a tumor or a metastatic tumor removed or destroyed via surgery, chemotherapy, radiation therapy, immunotherapy, or a combination thereof. In one example, the subject is a human subject.

The immune cells can be from the peripheral blood of the subject, lymph organs of the subject, lymph fluids of the subject, tissues of the subject, organ or organs of the subject, or a combination thereof.

The immune cells can comprise tumor infiltrating lymphocytes (TILs) from a tumor of a subject, a xenograft tumor derived from a tumor of a subject, or a combination thereof, and the Cbl-b$^{-/-}$ TICs can be specific to a tumor of a subject. The Cbl-b$^{-/-}$ TICs can have tumor specific cytotoxicity mediated via TCR (T cell receptor). TILs are immune cells that can migrate into a tumor and typically can include T cells, NK cells, dendritic cells and macrophages in variable proportions. Typically, T cells are the most abundant cells in TILs.

A xenograft tumor can be produced by xeno-transplantation of a part of a tumor into a mammalian animal. For a xenograft human tumor, an animal can be humanized via conventional process known in the medical industry or research communities.

The immune cells can be isolated from blood samples or tumor specimens using gradient centrifugation with commercial media such as Percoll Density Centrifugation Media available from GE Healthcare Life Sciences. Specific lineage of immune cells can be isolated using affinity column or FACS (Fluorescence Activated Cell Sorting). For example, CD45$^+$ cells can be isolated from tumor specimens with a CD45 MicroBeads MACS® column available from Miltenyi Biotec Inc, San Diego, California, USA, under respect trademark. In another example, CD8$^+$ T cells can be stained with antibodies specific to CD8 and TCRβ (the T cell receptor B) and subsequently purified with FACS sorting as CD8$^+$ TCRβ$^+$ cells. Commercially available FACS devices, such as those from BD Biosciences (Becton, Dickinson and Company, Franklin Lakes, New Jersey, USA), can be suitable.

The genomic Cbl-b genes in immune cells can be inactivated by introducing into the immune cells a genomic modification component comprising a Cas9 protein and a sgRNA$^{Cbl-b}$ targeting genomic Cbl-b genes of immune cells, and wherein the genomic modification component is free from deoxyribonucleic acids exogenous to the immune cells and free from viral nucleic acids. The genomic Cbl-b genes in immune cells can also be inactivated by introducing into the immune cells a genomic modification component comprising a Cas9 protein and a crRNA/TracrRNA (also known as a cr:tracrRNA) targeting genomic Cbl-b genes of immune cells and wherein the genomic modification component is free from deoxyribonucleic acids exogenous to the immune cells and free from viral nucleic acids.

Cas9 protein, CRISPR (Clustered Regularly Interspaced Short Palindromic Repeats)-associated protein-9 nuclease, is an RNA-guided endonuclease that catalyzes site-specific cleavage of double stranded DNA by cleaving double stranded DNA at the site complimentary to the guide RNA (M. Jinek et al., Science, 337, 816, 2012. DOI: 10.1126/Science. 1225829). The CRISPR-Cas9 system has been used in genome editing in prokaryotic and eukaryotic cells, such as described in U.S. Pat. No. 8,697,359 and U.S. Patent Publication No. 2014/0068797. In these conventional CRISPR-Cas9 systems, an expression vector or a combination of vectors comprising a DNA fragment encoding for a single guide RNA (sgRNA) and a Cas9 gene encoding the Cas9 protein are introduced into host cells. The single guide RNA (sgRNA) functions to guide Cas9 to a specific genomic location enabling targeted genome editing. The Cas9 protein can be in its natural form or a form modified through genetic engineering. The Cas9 gene can be from *Streptococcus pyogenes*, or other organisms. For expression in eukaryotic cells, the expression vector or vectors can also have DNAs originated from bacteria or virus that provide gene expression regulations, such as promoters. For example, a CMV (cytomegalovirus) promoter is typically used. The expression vectors can typically contain DNA sequences from bacteria to allow for the vectors to propagate in bacteria.

Applicants of this invention unexpected discovered that a genomic modification component comprising a Cas9 protein and a sgRNA targeting a desired genomic gene, when introduced into eukaryotic cells, can achieve desired gene editing of the genomic gene alleles without the needs for expression vectors that comprise DNA exogenous to the eukaryotic cells and contain DNA or RNA originated from bacteria or virus.

The Cas9 protein suitable for this invention can be a modified recombinant Cas9 protein. In one embodiment, the modified recombinant Cas9 protein comprises a C-Terminal nuclear localization signal region of an unmodified Cas9 protein. In an example, a modified Cas9 gene containing the C-Terminal nuclear localization signal region can be amplified using PCR (polymerase chain reaction) and cloned into an expression vector with a polyhistidine (His) tag protein to produce a His-tag fused Cas9 protein that allows for affinity purifications. Examples of the expression vectors with the His-tag can include commercially available pET28 plasmids His-Tag® (Clontech Laboratories, California, USA, under respective trademark). Other expression vectors having different protein tags for affinity purification, such as GST tag from the pGEX vectors available from GE Healthcare Life Sciences, can also be suitable for producing the modified recombinant Cas9 protein.

A sgRNA$^{Col-b}$ (single guide ribonucleic acid) targeting a specific site in the genomic Cbl-b gene locus of the immune cells can be designed to have a guide sequence of about 20 nucleotides (nt), such as in a range of from about 17 nts to about 28 nts in length that is homologous to a sequence located upstream of the RING finger domain of the Cbl-b gene to avoid the production of a mutant gene that results in a truncated dominate negative form of Cbl-b mutant protein. The guide sequence can be optimized to reduce the risk of off-target (OT) mutations. The guide sequence can be 20 nts in length and selected to have 80% to 100% homology to the Cbl-b gene based on the total length of the guide sequence and have the minimum mismatch to other regions in the entire genome of a subject. The guide sequence can have 5 to 0 mismatches in an entire genome of a subject, such as the human genome, in one example, 3 to 0 mismatches in another example, 1 to 0 mismatch in yet another example and 0 mismatch in a further example. The sgRNA$^{Cbl-b}$ can comprise a nucleic acid sequence GAGGUC-CACCAGAUUAGCUCUGG (Seq. No. 1), a nucleic acid sequence having homology in a range of from 80% to 100% to the sequence of said Seq. No. 1, or a combination thereof. When designing the sgRNA$^{Cbl-b}$, off-target (OT) mutations are considered in order to minimize the possibility of OT. In a particular example, the sgRNA$^{Col-b}$ comprises a nucleic acid sequence GAGGUCCACCAGAUUAGCUCUGG.

Once the sequence of sgRNA$^{Cbl-b}$ targeting the genomic Cbl-b gene is selected, it can be produced by chemically synthesized and purified such as by performance liquid chromatography (HPLC). The sequence of sgRNA$^{Col-b}$ can be cloned into a vector using various commercially available cloning and expressing vector systems, such as ones from CELLUTRON Life Tech, GE Dharmacon, (Lafayette, CO, USA) or QIAGEN (QIAGEN GmbH, Hilden, Germany). The produced sgRNA$^{Col-b}$ can be purified. The sgRNA$^{Col-b}$ targeting the genomic Cbl-b gene can also be produced via in vitro transcription using a template such as the Cbl-b gene DNA, or a PCR amplified genomic Cbl-b gene DNA. Commercially available MEGAshortscript T7 kit (Life Technologies) can be suitable.

The genomic modification component comprising the Cas9 protein and the sgRNA$^{Col-b}$ targeting the genomic Cbl-b genes can be introduced into immune cells by transfection, electroporation or microinjection to produce modified immune cells that can comprise modified T cells, modified NK cells, or a combination thereof. In one embodiment, the genomic modification component comprising the Cas9 protein and the sgRNA$^{Cbl-b}$ can be electroporated into T cells, NK cells, or a combination thereof. T cells can include CD8$^+$ T cells and CD4$^+$ T cells. NK cells can include CD56$^+$ NK cells, CD16$^+$ NK cells, or a combination thereof. The efficiency of Cbl-b gene inactivation and the subsequent loss of Cbl-b protein expression can be measured by intracellular staining with anti-Cbl-b antibody and analyzed by FACS, by a Surveyor assay using a SURVEYOR® mutation detection kit (available from Integrated DNA Technologies, Skokie, Illinois, USA, under respective trademark), by other DNA based analysis methods such as PCR, or a combination thereof. The modified mixed immune cells can have the Cbl-b gene inactivation in a range of from about 5% to about 90% of the total modified mixed immune cells in one example, in a range of from about 5% to about 60% in another example, in a range of from about 5% to about 40% in yet another example, in a range of from about 5% to about 20% in a further example, and in a range of from about 20% to about 50% in yet a further example, percentage based on the total detectable Cbl-b genes. For example, the proportion of wild type intact and cleaved mismatched DNA fragments of the Cbl-b gene can be calculated based on densities of the detectable bands or peaks. The percentage of the cleaved DNA indicates the proportion of the inactivated Cbl-b alleles in the cells.

Various functional assays can be performed to determine cell proliferation, immune cells toxicity to tumor cells, or other functions. Assays or tests that are commonly used now or newly developed in future can also be suitable.

This disclosure is further directed to a method for producing Cbl-b/tumor inhibiting cells (Cbl-b$^{-/-}$ TICs), the method comprising the steps of:

a) inactivating genomic Cbl-b genes of immune cells to produce the Cbl-b$^{-/-}$ TICs, wherein the Cbl-b$^{-/-}$ TICs are free from Cbl-b bio-function and free from deoxyribonucleic acids exogenous to the immune cells and free from viral nucleic acids exogenous to the immune cells.

As described above, the genomic Cbl-b genes can be inactivated by introducing into the immune cells a genomic modification component comprising a Cas9 protein and a sgRNA$^{Col-b}$ targeting the genomic Cbl-b genes of the immune cells, and wherein the genomic modification component is free from deoxyribonucleic acids exogenous to the immune cells and free from viral nucleic acids.

The immune cells can comprise unmodified T cells, unmodified NK cells, or a combination thereof. The immune cells can also comprise purified unmodified CD8$^+$ T cells, CD56$^+$ NK cells, CD16$^+$ NK cells, or a combination thereof.

As described above, immune cells can be from peripheral blood of a subject, lymph organs of the subject, lymph fluids of the subject, other organs or tissues of the subject, or a combination thereof; can be tumor infiltrating lymphocytes (TILs) from a tumor of the subject, a xenograft tumor derived from a tumor of the subject, or a combination thereof. The xenograft tumor can be produced by xenotransplantation of a part of a tumor into a mammalian animal as disclosed herein.

The method can comprise additional steps of isolating and expanding the tumor infiltrating lymphocytes (TILs) of the subject to produce the immune cells prior to inactivating the Cbl-b genes. The TILs can contain mostly tumor specific T cells, including CD4 helper and CD8 cytotoxic T cells. The TILs can be isolated and expanded as described hereafter.

The Cbl-b/tumor inhibiting cells (Cbl-b$^{-/-}$ TICs) of this invention modified from tumor-specific immune cells, such as the TILs mentioned herein, can inhibit one or more specific tumor or tumors including the tumor where the TILs are isolated from. In one example, Cbl-b$^{-/-}$ TICs produced from TILs isolated from a breast cancer of a subject can specifically inhibit a primary breast cancer of the subject. In another example, Cbl-b$^{-/-}$ TICs produced from TILs isolated from a breast cancer of a subject can specifically inhibit one or more metastatic tumors in the subject.

In one embodiment of this disclosure as directed to a method for producing Cbl-b$^{-/-}$ tumor inhibiting cells (Cbl-b$^{-/-}$ TICs), the method comprising the steps of:

a) inactivating genomic Cbl-b genes of immune cells to produce the Cbl-b$^{-/-}$ TICs, wherein the Cbl-b$^{-/-}$ TICs are free from Cbl-b bio-function and free from deoxyribonucleic acids exogenous to the immune cells and free from viral nucleic acids exogenous to the immune cells, wherein said immune cells are tumor infiltrating lymphocytes (TILs) isolated from a tumor of a subject, and optionally expanded.

In a further embodiment, the immune cells are tumor infiltrating T cells isolated from a tumor of a subject, and optionally expanded. Any method disclosed herein for isolating and optionally expanding immune cells including T cells can be suitable.

The Cbl-b$^{-/-}$ TICs can comprise Cbl-b$^{-/-}$ CD8$^+$ T cells, Cbl-b$^{-/-}$ NK cells, or a combination thereof. In another example, the Cbl-b$^{-/-}$ TICs can comprise Cbl-b$^{-/-}$ NK cells.

In yet another example, Cbl-b$^{-/-}$ TICs can comprise Cbl-b$^{-/-}$ TILs of the CD8$^+$ T cells or NK cells.

The Cbl-b$^{-/-}$ TICs can comprise Cbl-b$^{-/-}$ CD8$^+$ T cells in a range of from 10% to 100% in one example, 30% to 100% in another example, 50% to 100% in yet another example, 75% to 100% in a further example, and 85% to 100% in yet a further example, percentage based on total population of the Cbl-b$^{-/-}$ TICs. The Cbl-b$^{-/-}$ CD8$^+$ T cells are free from deoxyribonucleic acids exogenous to the subject and free from viral nucleic acids exogenous to the subject.

The Cbl-b$^{-/-}$ TICs can comprise the Cbl-b$^{-/-}$ NK cells in a range of from 10% to 100% in one example, 30% to 100% in another example, 50% to 100% in yet another example, 75% to 100% in a further example, and 85% to 100% in yet a further example, percentage based on total population of the Cbl-b$^{-/-}$ TICs. The Cbl-b$^{-/-}$ NK cells are free from deoxyribonucleic acids exogenous to the subject and free from viral nucleic acids exogenous to the subject.

The Cbl-b$^{-/-}$ NK cells can also be CD3, and can be preferred. The Cbl-b$^{-/-}$ TICs can comprise Cbl-b$^{-/-}$ CD3-CD56$^+$ NK cells, Cbl-b$^{-/-}$ CD3-CD16$^+$ NK cells, or a combination thereof.

As described above, the genomic modification component comprising the Cas9 protein and the sgRNA$^{Cbl-b}$ targeting the genomic Cbl-b genes can be introduced into the immune cells by transfection, electroporation or microinjection. Any of the aforementioned Cas9 protein and the sgRNA$^{Col-b}$ targeting the genomic Cbl-b genes are suitable.

The method can further comprise the steps of:

b) propagating the Cbl-b$^{-/-}$ TICs in in vitro cell culture; and c) harvesting the Cbl-b$^{-/-}$ TICs from the in vitro cell culture.

The Cbl-b$^{-/-}$ CD8$^+$ T cells can be propagated an in vitro culture system supported by growth factors IL-2, IL-15, TGF-β, or a combination thereof. In one embodiment, Cbl-b$^{-/-}$ CD8$^+$ T cells can be expanded for about 104 folds.

Inactivation of Cbl-b can allow NK cells to kill tumor cells more efficiently (M. Paolino, et al., Nature, Vol. 507, Page 508, Mar. 27, 2014. DOI: 10.1038/Nature12998). NK cells can be expanded via in vitro cell culture as described in detail by S. Carlens, et al. (Human Immunology 62, 1092-1098, 2001), herein incorporated by reference. In brief, immune cells containing NK cells can be cultured in serum-free medium supplemented with IL-2.

The Cbl-b$^{-/-}$ CD8$^+$ T cells, Cbl-b$^{-/-}$ NK cells, or a combination thereof, as disclosed herein, can be purified and harvested. Cbl-b$^{-/-}$ CD8$^+$ T cells can be purified and harvested by magnate column sorting (MACS) or FACS as described above. Cbl-b$^{-/-}$ CD8$^+$ T cells can also be enriched by cultivation of the total CD8$^+$ T cells in the presence of TGFβ. Cbl-b$^{-/-}$ CD16$^+$ NK cells and Cbl-b$^{-/-}$ CD56$^+$ NK cells can be purified and harvested by MACS or FACS. In one example, the NK cells are stained with fluorochrome-conjugated monoclonal anti-CD16 and anti-CD56 antibodies and subsequently sorted with FACS. Antibodies from Becton-Dickinson (Becton, Dickinson and Company, Franklin Lakes, New Jersey, USA) can be suitable. The Cbl-b$^{-/-}$ CD3 CD56$^+$ NK cells and Cbl-b$^{-/-}$ CD3-CD16$^+$ NK cells can be purified and harvested with staining using anti-CD3, anti-CD16 and anti-CD56 antibodies.

This disclosure is further directed to a method for treating a tumorous condition of a subject, the method comprising the steps of:

a) inactivating genomic Cbl-b genes of immune cells of the subject to produce Cbl-b/tumor inhibiting cells (Cbl-b$^{-/-}$ TICs), wherein the Cbl-b$^{-/-}$ TICs have inac-tivated Cbl-b gene alleles and are free from Cbl-b bio-function, and wherein the Cbl-b$^{-/-}$ TICs are free from deoxyribonucleic acids exogenous to the immune cells and free from viral nucleic acids exogenous to the immune cells;

b) optionally, propagating the Cbl-b$^{-/-}$ TICs in in vitro cell culture; and c) administering the Cbl-b$^{-/-}$ TICs to the subject.

As described above, immune cells can be isolated from the subject and can be from peripheral blood of the subject, lymph organs of the subject, lymph fluids of the subject, other organs or tissues of the subject, or a combination thereof. The immune cells can also be tumor infiltrating lymphocytes (TILs) from a tumor of the subject, a xenograft tumor derived from the tumor of the subject, or a combination thereof, and the Cbl-b$^{-/-}$ TICs are specific to a tumor of the subject. As mentioned herein, the Cbl-b$^{-/-}$ TICs can have tumor specific cytotoxicity that can be mediated via TCR (the T cell receptor). The subject can be a human subject. The subject can be a patient who has already developed a tumor. The subject can also be a person who is free from tumor at the time the immune cells are isolated.

The method can comprise additional steps of Isolating and expanding the tumor infiltrating lymphocytes (TILs) of the subject that contain mostly tumor specific T cells, including CD4$^+$ helper and CD8$^+$ cytotoxic T cells prior to inactivating the Cbl-b genes.

The genomic Cbl-b genes can be inactivated by introducing into the immune cells a genomic modification component comprising a Cas9 protein and a sgRNA$^{Cbl-b}$ targeting the genomic Cbl-b genes of the immune cells, and wherein the genomic modification component is free from deoxyribonucleic acids exogenous to the immune cells and free from viral nucleic acids.

Any of the aforementioned Cas9 protein can be suitable. The Cas9 protein can be a modified recombinant Cas9 protein comprising a C-Terminal nuclear localization signal region of an unmodified Cas9 protein.

The Cbl-b. TICs can comprise Cbl-b$^{-/-}$ CD8$^+$ T cells, Cbl-b$^{-/-}$ NK cells, or a combination thereof. In one example, the Cbl-b$^{-/-}$ TICs can comprise Cbl-b/CD8$^+$ T cells. The Cbl-b$^{-/-}$ TICs can comprise any of aforementioned Cbl-b$^{-/-}$ CD8$^+$ T cells, the Cbl-b$^{-/-}$ NK cells, or a combination thereof.

It is known that tumor antigen-specific cytotoxic T lymphocytes can be present within tumors of patients. The immune cells isolated from a tumor of a subject (patient) can be preferred since these immune cells contain tumor-specific CD8$^+$ T cells or NK cells that can be modified to produce Cbl-b 1. TICs that are specific to the tumor of the subject, meaning that the Cbl-b$^{-/-}$ TICs can have tumor antigen-specific cytotoxicity.

The Cbl-b$^{-/-}$ TICs can be administrated to the subject by injection, infusion or a combination thereof. In one example, Cbl-b$^{-/-}$ TICs can be directly injected into a tumor or to a specific tissue or area surrounding a tumor of a subject. In another example, Cbl-b$^{-/-}$ TICs can be intravenously infused into a subject. In a further example, Cbl-b$^{-/-}$ TICs can be injected and infused to a subject. The combination of injection and infusion can be particularly useful to treat an original tumor at one location, such as its primary site and one or more metastatic tumors in different locations in a subject. Typically, $0.5 \times 10^9$ to $5 \times 10^{10}$ cells in one example, $0.5 \times 10^8$ to $5 \times 10^{10}$ in another example, $0.5 \times 10^7$ to $5 \times 10^{10}$ in yet another example, $0.5 \times 10^7$ to $5 \times 10^8$, in a further example, $0.5 \times 10^7$ to $5 \times 10^9$ in yet another example, can be used to infuse into the subject. In further examples, $1 \times 10^5$ to $5 \times 10^7$ cells/kg (kilogram) subject bodyweight can be used to infuse into the subject.

A schematic diagram of an example of a process and the use of the modified immune cells to treat a subject are shown in FIG. 1. Tumor specimen can be surgically removed from the subject following approved procedures. TILs can be purified as disclosed hereafter and modified to inactivate the Cbl-b gene in vitro to produce Cbl-b$^{-/-}$ TICs. The modified Cbl-b$^{-/-}$ TICs can then be expanded in vitro and subsequently infused into the subject. The modified Cbl-b$^{-/-}$ TICs can also be infused into the subject directly without expansion in vitro.

The Cbl-b$^{-/-}$ TICs can be stored and cryopreserved in liquid nitrogen. The stored Cbl-b$^{-/-}$ TICs can be thawed and administrated to the subject. A pharmaceutical acceptable carrier including one or more inactive drug ingredients and a "GRAS" (Generally Recognized As Safe) material that are approved by US Food and Drug Administration (FDA) for human uses, plasma from the subject patient, blood or part thereof of the subject patient, or a combination thereof, can be mixed with the Cbl-b$^{-/-}$ TICs before or during administrating the Cbl-b$^{-/-}$ TICs into the subject.

A xenograft tumor can be produced by xeno-transplantation of a part of the tumor into a mammalian animal.

A xenograft tumor can be produced by a process comprising the steps of:

A) dispersing a part of a tumor into a tumor cell suspension;

B) optionally purifying tumor cells from the tumor cell suspension with one or more selected markers to produce purified tumor cells; and C) transplanting the tumor cell suspension or the purified tumor cells into a mammalian animal to form a xenograft tumor.

For a xenograft tumor produced from a human tumor, commercially available humanized animals can be used. For a solid tumor or non-solid tumor, a part of the tumor or a tumor-bearing tissue can be sectioned or diced into small tissue pieces, such as in sizes of in a range of from 0.5 mm to 5 mm in one example, 0.5 mm to 2 mm in another example, 0.5 mm to 1 mm in yet another example, in a largest dimension of the tissue pieces, then digested with enzymes, such as collagenases. The digested tissue pieces can be physically dispersed, such as by pipetting, into a tumor cell suspension.

For cells from some tumors or tumor stem cells, a further purification can be performed with selected markers. In one example, breast cancer stem cells (CSC) can be purified by staining with antibodies specific for blood cell lineages (Lin) markers, such as CD44 and CD24, and FACS sorting to obtain CD44$^+$/CD24$^{-/lo}$ Lin$^-$ cells. The Lin designates cells that are lineage markers negative. Blood cell lineage markers can include CD2, CD3, CD10, CD16, CD18, CD31, CD64 and CD140b. About 1000 enriched breast CSC can generate xenograft tumors in an immuno-deficient mouse, such as NOD SCID mouse. Detailed process is described by Al-Hajj M, et al. (Proceedings of the National Academy of Sciences, 100:3983-3988, 2003), herein incorporated by reference.

Tumor cell suspension or purified tumor cells, such as purified CSC, can be transplanted into mammary fat pads of NOD SCID mice to establish one or more xenograft tumors. Commercially available NOD SCID mice, such as the NOD scid gamma (NSG™ under respective trademark) mice from the Jackson Laboratory (Bar Harbor, ME USA, under respective trademark) can be suitable. Tumor cell suspension or purified tumor cells can also be cryostored, such as stored in liquid nitrogen, for later usage.

Mammalian animals can be selected from mice, rats, goats, rabbits, pigs, sheep, guinea pig, horses, dogs, camels, llamas, lama or alpaca. Any other animals that are suitable for xenograft can also be used. Immuno-deficient animal can be preferred. Immuno-deficient mice, such as nude mice and rats, SCID (severe combined immunodeficiency) mice, NOD (non-obese diabetic) mice, or NOD SCID mice can be further preferred.

TILs in xenograft tumor can be isolated for producing Cbl-b$^{-/-}$ TICs as described in this disclosure. The xenograft tumor can be used to produce large amounts of TILs for the production of Cbl-b$^{-/-}$ TICs including Cbl-b$^{-/-}$ T cells, Cbl-b$^{-/-}$ NK cells, or a combination thereof.

In one embodiment, the method for producing Cbl-b$^{-/-}$ tumor inhibiting cells (TICs) can comprise the steps of:

a) producing a xenograft tumor by dispersing a part of a tumor of a subject into a tumor cell suspension, optionally purifying tumor cells from the tumor cell suspension with one or more selected markers to produce purified tumor cells, and transplanting the tumor cell suspension or the purified tumor cells into a mammalian animal to form the xenograft tumor;

b) obtaining tumor infiltrating lymphocytes (TILs) from the xenograft tumor;

c) inactivating genomic Cbl-b genes of the TILs to produce the Cbl-b$^{-/-}$ TICs, wherein the Cbl-b$^{-/-}$ TICs are free from Cbl-b bio-function and free from deoxyribonucleic acids exogenous to the tumor infiltrating lymphocytes and free from viral nucleic acids, wherein the genomic Cbl-b genes are inactivated by introducing into the TILs a genomic modification component comprising a Cas9 protein and a sgRNA$^{Cbl-b}$ targeting the genomic Cbl-b genes of the TILs, and wherein the genomic modification component is free from deoxyribonucleic acids exogenous to the TILs and free from viral nucleic acids.

An animal bearing a xenograft tumor, herein referred to as "xenograft tumor animal", can be used as a model for testing the efficiency of Cbl-b$^{-/-}$ TICs. Cbl-b$^{-/-}$ TICs can be infused into a xenograft tumor animal. Aforementioned immune-deficient animals, such as immune-deficient mice, can be suitable. Regression of xenograft tumor in animals can be monitored after infusion of Cbl-b$^{-/-}$ TICs. Since the animals are immune-deficient, the infused Cbl-b$^{-/-}$ TICs are typically not rejected by animals' immune systems.

This disclosure is further directed to a method for producing Cbl-b$^{-/-}$ tumor inhibiting cells (TICs), the method comprising the steps of:

a) inactivating genomic Cbl-b genes of immune cells of a subject to produce the Cbl-b$^{-/-}$ TICs, wherein the Cbl-b$^{-/-}$ TICs are free from Cbl-b bio-function and free from deoxyribonucleic acids exogenous to the immune cells and free from viral nucleic acids, wherein the genomic Cbl-b genes are inactivated by introducing into the immune cells a genomic modification component comprising a Cas9 protein and a sgRNA$^{Cbl-b}$ targeting the genomic Cbl-b genes of the immune cells, and wherein the genomic modification component is free from deoxyribonucleic acids exogenous to the immune cells and free from viral nucleic acids.

b) optionally propagating the Cbl-b$^{-/-}$ TICs in in vitro cell culture;

c) optionally harvesting the Cbl-b$^{-/-}$ TICs from the in vitro cell culture; and d) determining anti-tumor efficiency of the Cbl-b$^{-/-}$ TICs by infusing the Cbl-b$^{-/-}$ TICs into a xenograft tumor animal having a xenograft tumor to produce anti-tumor efficiency data of the Cbl-b$^{-/-}$ TICs, wherein the xenograft tumor is derived from a tumor of the subject.

The Cbl-b$^{-/-}$ TICs can comprise any of aforementioned Cbl-b-CD8$^+$ T cells, Cbl-b$^{-/-}$ NK cells, or a combination thereof.

The xenograft tumor can be produced as described herein. Any of the aforementioned immune-deficient animals can be suitable. Immune-deficient mice can be preferred.

Applicant observed that mutations of the Cbl-b gene cannot be achieved efficiently by electroporation of the plasmid DNA or mRNA encoding a Cas9 protein in human primary T cells. Applicant unexpectedly discovered that using purified recombinant Cas9 protein complexed with an in vitro transcribed sgRNA$^{Cbl-b}$ can achieve efficient inactivation of the Cbl-b gene in human primary T cells and have less toxicity. This unexpected discovery by the Applicant provides many advantages as described herein and hereafter.

One advantage of this invention is that, the Cbl-b$^{-/-}$ TICs including the Cbl-b$^{-/-}$ CD8$^+$ T cells, the Cbl-b$^{-/-}$ NK cells, or a combination thereof, are free from deoxyribonucleic acids exogenous to the TICs (therefore, the subject) and free from viral nucleic acids. Unlike currently available gene-modified cell therapy, including CAR-T therapy and CRISPR mediated genome editing therapy that require introducing into the cells with at least one expression vector containing exogenous DNA and viral DNA or RNA, a pharmaceutical composition comprising the Cbl-b$^{-/-}$ TICs of this invention can provide immunotherapy without introducing exogenous DNA, viral DNA or viral RNA into patients, without the needs for transduction with virus or viral vectors, and therefore avoid any known and unknown potential risks in patients associated with the exposure to those exogenous genetic materials.

Another advantage of this invention is that in vitro genome modified Cbl-b$^{-/-}$ TICs do not express any foreign proteins, therefore, will not evoke immune responses by the immune system of the subject that can sabotage or otherwise having negative impact to Cbl-b$^{-/-}$ TICs. The current CRISPR mediated genome editing employs an expression vector that stably expresses the Cas9 protein in cells of the subject. The subject's own immune system can mount immune responses against the foreign protein Cas9, thus, can destroy Cas9-expressing genome-modified cells and pose a health risk to the subject receiving the treatment. Cbl-b$^{-/-}$ TICs of this invention are generated by the Cas9-sgRNA$^{Cbl-b}$ ribonucleoprotein complex that can be quickly degraded in T cells. Because Cbl-b$^{-/-}$ TICs of this invention do not express the Cas9 protein and therefore, the subject's own immune system will not react against Cbl-b$^{-/-}$ TICs or evoke potentially harmful responses to the subject receiving the Cbl-b$^{-/-}$ TICs for tumor therapy.

Yet another advantage of this invention is that Cbl-b$^{-/-}$ TICs provide personalized medicine for treating tumors. The Cbl-b$^{-/-}$ TICs of this invention isolated from the subject have the T cell receptor (TCR) that can recognize One or more epitopes on cells of the tumor but not of normal organs and tissues, therefore, Cbl-b$^{-/-}$ TICs of this invention can mount T cell responses specifically against the tumor of the subject without cytotoxicity to normal tissues or cells. Cbl-b$^{-/-}$ TICs of this invention can also be used to treat tumors in a different subject, for example a subject that has the same or similar immune compatibility, such as compatible MHC.

Yet another advantage of this invention is that Cbl-b$^{-/-}$ TICs are highly enriched for tumor specific CD4$^+$ and CD8$^+$ T cells, so that autoimmune responses can be maximally minimized.

Yet another advantage of this invention is that, unlike T cells in the CAR-T therapy that recognize a particular epitope of one tumor antigen, Cbl-b$^{-/-}$ TICs of this invention can have a broad spectrum of tumor-antigen specificities that are suitable for targeting many different types of tumors, such as solid or non-solid tumors that are of different origins with different oncogenes and in various organ locations. In one example, Cbl-b$^{-/-}$ TICs produced from a human patient subject can be used to treat the original tumor at its primary site and metastatic tumors in one or more different organs or locations. In a particular example, Cbl-b$^{-/-}$ TICs produced from a human patient subject can be used to treat the original tumor at its primary site and metastatic tumors in two or more different organs or locations. As used herein, metastatic tumors in two or more different organs or locations can be detected or identified by CT scans.

Yet another advantage of this invention is that the broad spectrum of tumor-antigen specificities of Cbl-b$^{-/-}$ TICs enables Cbl-b$^{-/-}$ TICs to target tumors that have lost one or more epitopes of tumor antigens, thus surpassing currently available therapies, such as the CAR-T therapy that only recognizes a single epitope of a tumor antigen that can lead to evasion of tumor cells that have lost a particular epitope.

Yet another advantage of this invention is that the Cbl-b gene product controls several immune suppressive pathways, including TGFβ, PD1/PD-L1, CTLA-4 and other checkpoint inhibitors. Cbl-b$^{-/-}$ TICs can be used to treat tumors that bear one or more of these suppressive biomarkers in one example and two or more of these suppressive biomarkers in another example.

Another advantage of this invention is that the Cbl-b$^{-/-}$ TICs can comprise Cbl-b$^{-/-}$ CD8$^+$ T cells that can be enriched and propagated in the presence of IL-2, IL-15, TGFβ and checkpoint inhibitors such as PD-1, PD-L1, or a combination thereof, so large amount of tumor inhibiting cells can be generated for the use in cancer immunotherapy.

Yet another advantage of this invention is that the Cbl-b$^{-/-}$ TICs can be expanded in vivo as demonstrated herein in Examples. A small number of the Cbl-b$^{-/-}$ TICs, such as in a range of from $1\times10^5$ to $1\times10^7$ cells/kg can be administered into a human subject and the cells can be expanded in vivo to deliver long lasing tumor inhibiting effect and to reduce potential cytotoxicity side effect that is often observed in current immune therapy approaches, such as CAR-T approach. The number of Cbl-b$^{-/-}$ TICs infused into a human subject can be in a range of from $0.1\times10^6$ to $0.5\times10^9$ cells in one example, $0.1\times10^6$ to $0.1\times10^9$ cells in another example, $0.1\times10^6$ to $0.5\times10^8$ cells in yet another example, $0.1\times10^6$ to $0.1\times10^8$ cells in yet another example, $0.1\times10^6$ to $0.5\times10^7$ cells in yet another example, $0.1\times10^6$ to $0.1\times10^7$ cells in yet another example, and $0.1\times10^6$ to $0.5\times10^6$ cells in yet another example. In a particular example, $5\times10^6$ cells can be administered into a subject. In yet further examples, the number of cells normalized based on a human subject's body weight, such as, $1\times10^5$ to $1\times10^7$ cells/kg can be suitable.

Cbl-b$^{-/-}$ TICs of this invention can be cryopreserved for future use. Cbl-b$^{-/-}$ TICs produced in any of aforementioned processes can be preserved for using in the future in the event of cancer recurrence in the subject.

Cbl-b$^{-/-}$ TICs produced in this invention may be used to treat aforementioned tumors and cancers including, but not limited to carcinomas, blastomas, sarcomas, melanomas, and hematologic cancers such as various leukemias, lymphoma, Hodgkin's disease, non-Hodgkin's lymphoma, myeloma, myelodysplasia and others. Examples of tumors that may be treated with the Cbl-b$^{-/-}$ TICs of this invention can include, but not limited to, acoustic neuroma, adenocarcinoma, brainstem glioma, mixed gliomas, basal cell carcinoma, bile duct carcinoma, bladder carcinoma, breast cancer, bronchogenic carcinoma, cervical cancer, choriocarcinoma, colon carcinoma, ependymoma, germinoma, glioblastoma astrocytoma, hemangioblastoma, hepatocellular carcinoma, hepatoma, lung cancers, lymphoid malignancy, medullary carcinoma, medullary thyroid carcinoma, medulloblastoma, melanoma, menangioma, neuroblastoma, oligodendroglioma, ovarian cancer, pancreatic cancer, papillary adenocarcinomas, papillary carcinoma, papillary thyroid carcinoma, pheochromocytomas, sebaceous gland carcinoma, pinealoma, prostate cancer, renal cell carcinoma, retinoblastoma and brain metastases, Schwannoma craniopharyogioma, seminoma, squamous cell carcinoma, sweat gland carcinoma, testicular tumor, other known tumors and tumors that are subsequently identified or diagnosed.

The Cbl proteins are members of a family of E3-ubiquitin ligases involved in various signaling pathways (See references list herein). Their roles in the immune system have been demonstrated previously in the Cbl and Cbl-b gene-targeted mice. It has been previously shown that one of the members of this family, Cbl-b, plays a critical role in regulating T cell activation. The Cbl-b/mutation disrupts at least three tumor suppressive pathways in T cells including TGFβ, CTLA4, and PD1/PD-L1 pathways, that block T cell mediated responses against tumors. There is evidence demonstrating that Cbl-b/mice are resistant to inoculated tumors and that adoptively transferred Cbl-b$^{-/-}$ CD8$^+$ T cells alone are sufficient to eradicate established tumors. Cbl-b$^{-/-}$ T cells also prevent the development of spontaneous lymphoma in ATM$^{-/-}$ or p53$^{-/-}$ mice and UV irradiation induced spontaneous skin cancers in mice. Previous studies have shown that Cbl-b deficient or knocked-down human T cells can be generated in human primary T cells by RNA interference methods using siRNA approach. However, the siRNA knockdown approach only temporarily suppresses Cbl-b expression, thus making it difficult to apply in tumor immunotherapy.

Applicant discovered that targeting the Cbl-b pathway can be a powerful approach to generate "super killer" T cells for cancer immunotherapy and that Cbl-b$^{-/-}$ T cells may recognize unknown tumor antigens expressed on emerging tumors. Applicant further discovered the process and the genomic modification component disclosed herein can achieve a long-lasting effect to permanently silence Cbl-b expression in human primary T cells with the aforementioned advantages.

This invention is further directed to a pharmaceutical composition comprising a population of tumor inhibiting cells (TICs) modified from immune cells, wherein the TICs comprise at least one inactivated genomic allele of at least one target gene and are free from bio-function of the target gene, and wherein said TICs are free from deoxyribonucleic acids exogenous to said immune cells and are free from viral nucleic acids exogenous to the immune cells.

The target gene can comprise Cbl-b, CTLA4, PD-1, LAG3, TIM3, CD73, KIR (killer inhibitory receptor), Fas (a member of the tumor necrosis factor (TNF)-receptor), AHR (aryl hydrocarbon receptor), Smad2, Smad4, TGFBR (TGF-beta receptor), ILT-3, or a combination thereof.

In one example, the TICs can comprise T cells, NK cells, or a combination thereof. In another example, the TICs can comprise Cbl-b$^{-/-}$ CD4$^+$ T cells, Cbl-b$^{-/-}$ CD8$^+$ T cells, Cbl-b$^{-/-}$ NK cells, PD-1$^{-/-}$ T cells, PD-1$^{-/-}$ NK cells, CTLA-4$^{-/-}$ T cells, CTLA4$^{-/-}$ NK cells, TIM-3$^{-/-}$ T cells, TIM-3$^{-/-}$ NK cells, KIP$^{-/-}$ T cells, KIR$^{-/-}$ NK cells, LAG3$^{-/-}$ T cells, LAG3$^{-/-}$ NK cells, CD73-T cells, CD73$^{-/-}$ NK cells, Fas$^{-/-}$ T cells, Fas$^{-/-}$ NK cells, AHR$^{-/-}$ T cells, AHR$^{-/-}$ NK cells, Smad2$^{-/-}$ T cells, Smad2$^{-/-}$ NK cells, Smad4$^{-/-}$ T cells, Smad4$^{-/-}$ NK cells, TGFBR$^{-/-}$ T cells, TGFBR$^{-/-}$ NK cells, ILT-3$^{-/-}$ T cells, ILT-3$^{-/-}$ NK cells, or a combination thereof. In the pharmaceutical composition disclosed herein, the TICs are histological compatible to a subject.

As disclosed herein, the immune cells can be from peripheral blood of the subject, lymph organs of the subject, lymph fluids of the subject, other organs or tissues of the subject, or a combination thereof. The immune cells can comprise tumor infiltrating lymphocytes (TILs) from a tumor of the subject, a xenograft tumor derived from a tumor of the subject, or a combination thereof, as disclosed above.

This invention is further directed to a method for producing tumor inhibiting cells (TICs), the method comprising the steps of:

a) inactivating at least one genomic allele of at least one target gene and of immune cells to produce the TICs that are free from bio-function of said target gene, wherein the TICs are free from deoxyribonucleic acids exogenous to the immune cells and free from viral nucleic acids exogenous to the immune cells;

wherein the at least one target gene comprises Cbl-b, CTLA4, PD-1, LAG3, TIM3, CD73, KIR (killer inhibitory receptor), Fas, AHR (aryl hydrocarbon receptor), Smad2, Smad4, TGFBR (TGFβ receptor), ILT-3, or a combination thereof.

As disclosed above, the genomic allele of the target gene can be inactivated by introducing into the immune cells a genomic modification component comprising a Cas9 protein and at least one sgRNA targeting at least one target gene of the immune cells, and wherein the genomic modification component is free from deoxyribonucleic acids exogenous to the immune cells and free from viral nucleic acids. Any of the Cas9 protein and sgRNA or a combination of sgRNAs disclosed above and hereafter can be suitable.

As disclosed above and hereafter, immune cells can comprise unmodified T cells, unmodified NK cells, or a combination thereof. Immune cells can also comprise purified unmodified T cells, purified unmodified NK cells, or a combination thereof. The purified T cells, NK cells disclosed above and hereafter can be suitable. The method for isolating and purification of T cells or NK cells disclosed above or hereafter can be suitable. Immune cells can comprise tumor infiltrating lymphocytes (TILs) from a tumor of a subject, a xenograft tumor derived from a tumor of a subject, or a combination thereof. The subject can be a human subject.

A xenograft tumor can be produced by xeno-transplantation of a part of a tumor of a subject into a mammalian animal, such as an immune-deficient mics, as disclosed above and hereafter.

The Cbl-b$^{-/-}$ TICs produced from the method disclosed herein can comprise Cbl-b$^{-/-}$ T cells including Cbl-b-CD4$^+$ T cells, Cbl-b$^{-/-}$ CD8$^+$ T cells, Cbl-b$^{-/-}$ NK cells, or a combination thereof. The Cbl-b$^{-/-}$ TICs can comprise in a range of from 5% to 100% of Cbl-b$^{-/-}$ T cells in one example, 10% to 100% of Cbl-b$^{-/-}$ T cells in another example, 15% to 100% of Cbl-b$^{-/-}$ T cells in yet another example, 20% to 100% of Cbl-b$^{-/-}$ T cells in yet another example, 40% to 100% of Cbl-b$^{-/-}$ T cells in yet another example, 50% to 100% of Cbl-b$^{-/-}$ T cells in one example, 60% to 100% of Cbl-b$^{-/-}$ T cells in yet another example, 70% to 100% of Cbl-b$^{-/-}$ T cells in yet another example, 80% to 100% of Cbl-b$^{-/-}$ T cells in yet another example, 90% to 100% of Cbl-b$^{-/-}$ T cells in yet another example and 95% to 100% of Cbl-b$^{-/-}$ T cells in an even another example, percentages based on total population of the Cbl-b$^{-/-}$ TICs. The Cbl-b$^{-/-}$ TICs can also comprise in a range of from 5% to 100% of Cbl-b$^{-/-}$ NK cells, 10% to 100% of Cbl-b-NK cells in another example, 15% to 100% of Cbl-b$^{-/-}$ NK cells in yet another example, 20% to 100% of Cbl-b$^{-/-}$ NK cells in yet another example, 40% to 100% of Cbl-b$^{-/-}$ NK cells in yet another example, 50% to 100% of Cbl-b-NK cells in one example, 60% to 100% of Cbl-b$^{-/-}$ NK cells in yet another example, 70% to 100% of Cbl-b$^{-/-}$ NK cells in yet another example, 80% to 100% of Cbl-b$^{-/-}$ NK cells in yet another example, 90% to 100% of Cbl-b-NK cells in yet another example and 95% to 100% of Cbl-b$^{-/-}$ NK cells in an even another example, percentages based on total population of the Cbl-b$^{-/-}$ TICs.

The method disclosed herein can further comprise the steps of:

b) propagating the TICs in in vitro cell culture; and c) harvesting the TICs from the in vitro cell culture.

Any of methods for propagating, harvesting, selecting and purifying TICs disclosed above and hereafter can be suitable.

This invention is further directed to a method for treating a tumorous condition of a subject in need thereof, the method comprising the steps of:

a) inactivating at least one genomic allele of at least one target gene of immune cells of the subject to produce tumor inhibiting cells (TICs) that are free from bio-function of said target gene, wherein the TICs are free from deoxyribonucleic acids exogenous to the immune cells and free from viral nucleic acids exogenous to the immune cells, wherein the target gene is selected from Cbl-b, CTLA4, PD-1, LAG3, TIM3, CD73, KIR (killer inhibitory receptor), Fas, AHR (aryl hydrocarbon receptor), Smad2, Smad4, TGFBR (TGFβ receptor), ILT-3, or a combination thereof;

b) optionally, propagating the TICs in in vitro cell culture; and c) administering the TICs to the subject.

The TICs can be free from bio-functions of at least two of the target genes. In one example, the TICs of this invention are free from bio-function of at least one of the target genes. In another example, the TICs of this invention are free from bio-functions of two or more target genes. Any combinations of the target genes can be suitable, such as, but not limited to, Cbl-b and one or more of the PD-1, CTLA4, LAG3, TIM3, CD73, KIR, Fas, AHR, Smad2, Smad4, TGFBR or ILT-3 in one example, PD-1 and one or more of the Cbl-b, CTLA4, LAG3, TIM3, CD73, KIR, Fas, AHR, Smad2, Smad4, TGFBR or ILT-3 in another example, CTLA4 and one or more of the PD-1, Cbl-b, LAG3, TIM3, CD73, KIR, Fas, AHR, Smad2, Smad4, TGFBR or ILT-3 in yet another example, and LAG3 and one or more of the PD-1, CTLA4, TIM3, CD73, KIR, Fas, AHR, Smad2, Smad4, TGFBR or ILT-3 in a further example.

As mentioned above, a genomic allele of a target gene can be inactivated by introducing into immune cells a genomic modification component comprising a Cas9 protein and at least one sgRNA targeting the target gene of the immune cells, wherein the genomic modification component is free from deoxyribonucleic acids exogenous to the immune cells and free from viral nucleic acids. The TICs can comprise Cbl-b$^{-/-}$ CD4$^+$ T cells, Cbl-b$^{-/-}$ CD8$^+$ T cells, Cbl-b$^{-/-}$ NK cells, PD-1$^{-/-}$ T cells, PD-1$^{-/-}$ NK cells, CTLA-4$^{-/-}$ T cells, CTLA4$^{-/-}$ NK cells, TIM-3$^{-/-}$ T cells, TIM-3$^{-/-}$ NK cells, KIP$^{-/-}$ T cells, KIR$^{-/-}$ NK cells, LAG3$^{-/-}$ T cells, LAG3$^{-/-}$ NK cells, CD73$^{-/-}$ T cells, CD73$^{-/-}$ NK cells, Fas$^{-/-}$ T cells, Fas$^{-/-}$ NK cells, AHR$^{-/-}$ T cells, AHR$^{-/-}$ NK cells, Smad2$^{-/-}$ T cells, Smad2$^{-/-}$ NK cells, Smad4$^{-/-}$ T cells, Smad4$^{-/-}$ NK cells, TGFBR$^{-/-}$ T cells, TGFBR$^{-/-}$ NK cells, ILT-3$^{-/-}$ T cells, ILT-3$^{-/-}$ NK cells, or a combination thereof. The immune cells can be from peripheral blood of the subject, lymph organs of the subject, lymph fluids of the subject, other organs or tissues of the subject or a combination thereof. The subject can be a human subject, such as a cancer patient. The TICs can be administrated to the subject by injection, infusion or a combination thereof. The immune cells can be tumor infiltrating lymphocytes (TILs) from a tumor of the subject, a xenograft tumor derived from the tumor of the subject, or a combination thereof. The xenograft tumor can be produced by xeno-transplantation of a part of the tumor of the subject into a mammalian animal, for example a mouse or an immune-deficient mouse.

Target sgRNAs for a checkpoint gene CTLA4 can be designed according to the "Design of the Cbl-b targeting sgRNA" described herein. Commercial tools and guidelines, such as those available at CLONETECH (www.clontech.com) can also be utilized. The Cas9 protein can be mixed with one or more of the sgRNAs for transfecting immune cells or TILs. Efficiency of gene targeting/deletion can be assayed as described herein.

Target sgRNAs for another checkpoint gene PD-1 can be designed according the "Design of the Cbl-b targeting sgRNA" described herein. Commercial tools and guidelines, such as those available at CLONETECH (www.clontech.com) can also be utilized. The Cas9 protein can be mixed with one or more of the sgRNAs for transfecting immune cells or TILs. Efficiency of gene targeting/deletion can be assayed as described herein.

Target sgRNAs for another checkpoint gene LAG3 can be designed according the "Design of the Cbl-b targeting sgRNA" described herein. Commercial tools and guidelines, such as those available at CLONETECH (www.clontech.com) can also be utilized. The Cas9 protein can be mixed with one or more of the sgRNAs for transfecting immune cells or TILs. Efficiency of gene targeting/deletion can be assayed as described herein.

Target sgRNAs for another checkpoint gene TIM3 can be designed according the "Design of the Cbl-b targeting sgRNA" described herein. Commercial tools and guidelines, such as those available at CLONETECH (www.clontech.com) can also be utilized. The Cas9 protein can be mixed with one or more of the sgRNAs for transfecting immune cells or TILs. Efficiency of gene targeting/deletion can be assayed as described herein.

Target sgRNAs for yet another checkpoint genes CD73 can be designed according the "Design of the Cbl-b targeting sgRNA" described herein. Commercial tools and guidelines, such as those available at CLONETECH (www.clontech.com) can also be utilized. The Cas9 protein can be mixed with one or more of the sgRNAs for transfecting immune cells or TILs. Efficiency of gene targeting/deletion can be assayed as described herein.

Target sgRNAs for yet another checkpoint genes KIR can be designed according the "Design of the Cbl-b targeting sgRNA" described herein. Commercial tools and guidelines, such as those available at CLONETECH (www.clontech.com) can also be utilized. The Cas9 protein can be mixed with one or more of the sgRNAs for transfecting immune cells or TILs. Efficiency of gene targeting/deletion can be assayed as described above.

Target sgRNAs for yet another checkpoint genes Fas can be designed according the "Design of the Cbl-b targeting sgRNA" described herein. Commercial tools and guidelines, such as those available at CLONETECH (www.clontech. com) can also be utilized. The Cas9 protein can be mixed with one or more of the sgRNAs for transfecting immune cells or TILs. Efficiency of gene targeting/deletion can be assayed as described herein.

Target sgRNAs for yet another checkpoint genes AHR can be designed according the "Design of the Cbl-b targeting sgRNA" described herein. Commercial tools and guidelines, such as those available at CLONETECH (www.clontech. com) can also be utilized. The Cas9 protein can be mixed with one or more of the sgRNAs for transfecting immune cells or TILs. Efficiency of gene targeting/deletion can be assayed as described herein.

Target sgRNAs for yet another checkpoint genes Smad2 can be designed according the "Design of the Cbl-b targeting sgRNA" described herein. Commercial tools and guidelines, such as those available at CLONETECH (www.clontech. com) can also be utilized. The Cas9 protein can be mixed with one or more of the sgRNAs for transfecting immune cells or TILs. Efficiency of gene targeting/deletion can be assayed as described herein.

Target sgRNAs for yet another checkpoint genes Smad4 can be designed according the "Design of the Cbl-b targeting sgRNA" described herein. Commercial tools and guidelines, such as those available at CLONETECH (www.clontech. com) can also be utilized. The Cas9 protein can be mixed with one or more of the sgRNAs for transfecting immune cells or TILs. Efficiency of gene targeting/deletion can be assayed as described herein.

Target sgRNAs for yet another checkpoint genes TGFBR can be designed according the "Design of the Cbl-b targeting sgRNA" described herein. Commercial tools and guidelines, such as those available at CLONETECH (www.clontech. com) can also be utilized. The Cas9 protein can be mixed with one or more of the sgRNAs for transfecting immune cells or TILs. Efficiency of gene targeting/deletion can be assayed as described herein.

Target sgRNAs for yet another checkpoint genes ILT-3 can be designed according the "Design of the Cbl-b targeting sgRNA" described herein. Commercial tools and guidelines, such as those available at CLONETECH (www.clontech. com) can also be utilized. The Cas9 protein can be mixed with one or more of the sgRNAs for transfecting immune cells or TILs. Efficiency of gene targeting/deletion can be assayed as described herein.

The method disclosed herein can further comprise administering the subject one or more cancer drugs, one or more checkpoint inhibitors, additional one or more therapeutic agents, or a combination thereof. The cancer drugs, the checkpoint inhibitors, or a combination thereof can be administered to the subject prior to, during, or after administering the TICs. The cancer drugs, the checkpoint inhibitors, or a combination thereof can be administered to the subject in a range of from 1 to 10 days to about 10 minutes to about 20 hours prior to administering the TICs in one example, from 1 day to about 180 days prior to administering the TICs in another example, mixing together with the TICs during administering the TICs in yet another example, separately administering to the subject during administering the TICs in yet another example, in a few days to a few hours after administering the TICs in a further example and from 1 day to about 180 days after administering the TICs in an even further example. The cancer drugs, the checkpoint inhibitors, or a combination thereof can also be administered to the subject multiple times, such as a combination of prior, during and after administering the TICs. Cancer drugs can also be implanted into a subject, such as for controlled or localized release.

Suitable cancer drugs can include small molecule drugs, chemotherapy drugs, vaccines, large molecule drugs, or a combination thereof, and can be selected from cancer drugs listed by the National Institutes for Health (NIH) (URL for the NIH list: www.cancer.gov/about-cancer/treatment/ drugs) and available from various suppliers or any new cancer drugs developed and become available. Examples of the drugs can be a single drug or a combination of drugs and can include, but not limited to, such as Abemaciclib, Abiraterone Acetate, Abitrexate (Methotrexate), ABRAXANE® (Paclitaxel Albumin-stabilized Nanoparticle Formulation), ABVD (combination of A=Doxorubicin, Hydrochloride (Adriamycin), B=Bleomycin, V=Vinblastine Sulfate, and D=Dacarbazine), ABVE (A=Doxorubicin Hydrochloride (Adriamycin), B=Bleomycin, V=Vincristine Sulfate and E=Etoposide Phosphate), ABVE-PC (ABVE and P=Prednisone, C=Cyclophosphamide), AC (A=Doxorubicin Hydrochloride (Adriamycin), C=Cyclophosphamide), Acalabrutinib, AC-T (AC and T=Paclitaxel (Taxol)), ADCETRIS® (Brentuximab Vedotin), ADE (A=Cytarabine (Ara-C), D=Daunorubicin Hydrochloride and E=Etoposide Phosphate), Ado-Trastuzumab Emtansine, Adriamycin (Doxorubicin Hydrochloride), Afatinib Dimaleate, Afinitor (Everolimus), Akynzeo (Netupitant and Palonosetron Hydrochloride), Aldara (Imiquimod), Aldesleukin, Alecensa (Alectinib), Alectinib, Alemtuzumab, ALIMTA® (Pemetrexed Disodium), Aliqopa (Copanlisib Hydrochloride), Alkeran for Injection (Melphalan Hydrochloride), Alkeran Tablets (Melphalan), ALOXI® (Palonosetron Hydrochloride), Alunbrig (Brigatinib), Ambochlorin (Chlorambucil), Amboclorin (Chlorambucil), Amifostine, Aminolevulinic Acid, Anastrozole, Aprepitant, Aredia (Pamidronate Disodium), ARIMIDEX® (Anastrozole), Aromasin (Exemestane), Arranon (Nelarabine), Arsenic Trioxide, ARZERRA® (Ofatumumab), Asparaginase *Erwinia chrysanthemi*, Atezolizumab, AVASTIN® (Bevacizumab), Avelumab, Axicabtagene Ciloleucel, Axitinib, Azacitidine, BAVENCIO® (Avelumab), BEACOPP (B=Bleomycin, E=Etoposide Phosphate, A=Doxorubicin Hydrochloride (Adriamycin), C=Cyclophosphamide, O=Vincristine Sulfate (Oncovin), P=Procarbazine Hydrochloride and P=Prednisone), Becenum (Carmustine), Beleodaq (Belinostat), Belinostat, Bendamustine Hydrochloride, BEP, Besponsa (Inotuzumab Ozogamicin), Bevacizumab, Bexarotene, Bexxar (Tositumomab and Iodine I 131 Tositumomab), Bicalutamide, BiCNU (Carmustine), Bleomycin, Blinatumomab, BLINCYTO® (Blinatumomab), Bortezomib, BOSULIF® (Bosutinib), Bosutinib, Brentuximab Vedotin, Brigatinib, BuMel, Busulfan, BUSULFEX® (Busulfan), Cabazitaxel, CABOMETYX® (Cabozantinib-S-Malate), Cabozantinib-S-Malate, CAF (C=Cyclophosphamide, A=Doxorubicin Hydrochloride (Adriamycin) and F=Fluorouracil), CALQUENCE® (Acalabrutinib), CAMPATH® (Alemtuzumab), CAMPTOSAR® (Irinotecan Hydrochloride), Capecitabine, CAPOX (CAP=Capecitabine and OX=Oxaliplatin), CARAC® (Fluorouracil-Topical), Carboplatin, CARBOPLATIN-TAXOL, Carfilzomib, Carmubris (Carmustine), Carmustine, Carmustine Implant, CASODEX® (Bicalutamide), CEM (C=Carboplatin, E=Etoposide Phosphate and M=Melphalan Hydrochloride), Ceritinib, CERUBIDINE® (Daunorubicin Hydrochloride), CER-VARIX® (Recombinant HPV Bivalent Vaccine), Cetuximab, CEV (C=Carboplatin, E=Etoposide Phosphate, V=Vincristine Sulfate), Chlorambucil, CHLORAMBUCIL-PREDNISONE, CHOP (C=Cyclophosphamide, H=Doxorubicin Hydrochloride (Hydroxydaunomycin), O=Vincristine Sulfate (Oncovin), P=Prednisone), Cisplatin, Cladribine, Clafen (Cyclophosphamide), Clofarabine, CLO-FAREX® (Clofarabine), CLOLAR® (Clofarabine), CMF, Cobimetinib, COMETRIQ® (Cabozantinib-S-Malate), Copanlisib Hydrochloride, COPDAC (C=Cyclophosphamide, O=Vincristine Sulfate (Oncovin), P=Prednisone, DAC=Dacarbazine), COPP (C=Cyclophosphamide, O=Vincristine Sulfate (Oncovin), P=Procarbazine Hydrochloride, P=Prednisone), COPP-ABV, COSMEGEN® (Dactinomycin), COTELLIC® (Cobimetinib), Crizotinib, CVP, Cyclophosphamide, Cyfos (Ifosfamide), CYRAMZA® (Ramucirumab), Cytarabine, Cytarabine Liposome, Cytosar-U (Cytarabine), Cytoxan (Cyclophosphamide), Dabrafenib, Dacarbazine, DACO-GEN® (Decitabine), Dactinomycin, Daratumumab, DARZALEX® (Daratumumab), Dasatinib, Daunorubicin Hydrochloride, Daunorubicin Hydrochloride and Cytarabine Liposome, Decitabine, Defibrotide Sodium, DEFITE-LIO® (Defibrotide Sodium), Degarelix, Denileukin Diftitox, Denosumab, DepoCyt (Cytarabine Liposome), Dexamethasone, Dexrazoxane Hydrochloride, Dinutuximab, Docetaxel, DOXIL® (Doxorubicin Hydrochloride Liposome), Doxorubicin Hydrochloride, Doxorubicin Hydrochloride Liposome, Dox-SL (Doxorubicin Hydrochloride Liposome), DTIC-Dome (Dacarbazine), Durvalumab, EFUDEX® (Fluorouracil—Topical), ELITEK® (Rasburicase), ELLENCE® (Epirubicin Hydrochloride), Elotuzumab, ELOXATIN® (Oxaliplatin), Eltrombopag Olamine, Emend (Aprepitant), EMPLICITI® (Elotuzumab), Enasidenib Mesylate, Enzalutamide, Epirubicin Hydrochloride, EPOCH, EERBITUX® (Cetuximab), Eribulin Mesylate, Erivedge (Vismodegib), Erlotinib Hydrochloride, ERWINAZE® (Asparaginase *Erwinia chrysanthemi*), Ethyol (Amifostine), Etopophos (Etoposide Phosphate), Etoposide, Etoposide Phosphate, Evacet (Doxorubicin Hydrochloride Liposome), Everolimus, Evista (Raloxifene Hydrochloride), EVOMELA® (Melphalan Hydrochloride), Exemestane, 5-FU (Fluorouracil Injection), 5-FU (Fluorouracil—Topical), Fareston (Toremifene), FARYDAK® (Panobinostat), Faslodex (Fulvestrant), FEC (F=Fluorouracil, E=Epirubicin Hydrochloride, C=Cyclophosphamide), FEMARA® (Letrozole), Filgrastim, Fludara (Fludarabine Phosphate), Fludarabine Phosphate, Fluoroplex (Fluorouracil—Topical), Fluorouracil Injection, Fluorouracil—Topical, Flutamide, Folex (Methotrexate), Folex PFS (Methotrexate), FOLFIRI, FOLFIRI-BEVACIZUMAB, FOLFIRI-CETUXIMAB, FOLFIRINOX, FOLFOX, Folotyn (Pralatrexate), FU-LV (FU=Fluorouracil and LV=Leucovorin Calcium), Fulvestrant, Gardasil (Recombinant HPV Quadrivalent Vaccine), Gardasil 9 (Recombinant HPV Nonavalent Vaccine), GAZYVAR (Obinutuzumab), Gefitinib, Gemcitabine Hydrochloride, GEMCITABINE-CISPLATIN, GEMCITABINE-OXALIPLATIN, Gemtuzumab Ozogamicin, Gemzar (Gemcitabine Hydrochloride), GILOTRIF® (Afatinib Dimaleate), GLEEVEC® (Imatinib Mesylate), Gliadel (Carmustine Implant), Gliadel wafer (Carmustine Implant), Glucarpidase, Goserelin Acetate, HALAVEN® (Eribulin Mesylate), HEMANGEOL® (Propranolol Hydrochloride), HerceptinHERCEPTIN® (Trastuzumab), HPV Bivalent Vaccine, Recombinant, HPV Nonavalent Vaccine, Recombinant, HPV Quadrivalent Vaccine, Recombinant, HYCAMTIN® (Topotecan Hydrochloride), Hydrea (Hydroxyurea), Hydroxyurea, Hyper-CVAD, Ibrance (Palbociclib), Ibritumomab Tiuxetan, Ibrutinib, ICE (I=Ifosfamide, C=Carboplatin, E=Etoposide Phosphate), Iclusig (Ponatinib Hydrochloride), Idamycin (Idarubicin Hydrochloride), Idarubicin Hydrochloride, Idelalisib, DHIFA® (Enasidenib Mesylate), IFEX® (Ifosfamide), Ifosfamide, Ifosfamidum (Ifosfamide), IL-2 (Aldesleukin), Imatinib Mesylate, Imbruvica (Ibrutinib), Imfinzi (Durvalumab), Imiquimod, IMLYGIC® (Talimogene Laherparepvec), INLYTA® (Axitinib), Inotuzumab Ozogamicin, Interferon Alfa-2b, Recombinant, Interleukin-2 (Aldesleukin), Intron A (Recombinant Interferon Alfa-2b), Iodine I 131 Tositumomab and Tositumomab, Ipilimumab, IRESSA® (Gefitinib), Irinotecan Hydrochloride, Irinotecan Hydrochloride Liposome, ISTODAX® (Romidepsin), Ixabepilone, Ixazomib Citrate, IXEMPRA® (Ixabepilone), JAKAFI® (Ruxolitinib Phosphate), JEB (J=Carboplatin (JM8), E=Etoposide Phosphate, B=Bleomycin), JEVTANA® (Cabazitaxel), KADCYLA® (Ado-Trastuzumab Emtansine), Keoxifene (Raloxifene Hydrochloride), KEPIVANCE® (Palifermin), KEYTRUDA® (Pembrolizumab), Kisqali (Ribociclib), Kymriah (Tisagenlecleucel), Kyprolis (Carfilzomib), Lanreotide Acetate, Lapatinib Ditosylate, LARTRUVOR (Olaratumab), Lenalidomide, Lenvatinib Mesylate, LENVIMA® (Lenvatinib Mesylate), Letrozole, Leucovorin Calcium, LEUKERAN® (Chlorambucil), Leuprolide Acetate, Leustatin® (Cladribine), LEVULAN® (Aminolevulinic Acid), Linfolizin (Chlorambucil), LIPODOX® (Doxorubicin Hydrochloride Liposome), Lomustine, LONSURF® (Trifluridine and Tipiracil Hydrochloride), Lupron (Leuprolide Acetate), Lupron Depot (Leuprolide Acetate), Lupron Depot-Ped (Leuprolide Acetate), Lynparza (Olaparib), MARQIBO® (Vincristine Sulfate Liposome), MATULANE® (Procarbazine Hydrochloride), Mechlorethamine Hydrochloride, Megestrol Acetate, MEKINIST® (Trametinib), Melphalan, Melphalan Hydrochloride, Mercaptopurine, Mesna, MESNEX® (Mesna), Methazolastone (Temozolomide), Methotrexate, Methotrexate LPF (Methotrexate), Methylnaltrexone Bromide, Mexate (Methotrexate), Mexate-AQ (Methotrexate), Midostaurin, Mitomycin C, Mitoxantrone Hydrochloride, Mitozytrex (Mitomycin C), MOPP (M=Mechlorethamine Hydrochloride, O=Vincristine Sulfate (Oncovin), P=Procarbazine Hydrochloride, P=Prednisone), MOZOBIL® (Plerixafor), Mustargen (Mechlorethamine Hydrochloride), MUTAMYCIN® (Mitomycin C), MYLERAN® (Busulfan), MYLOSAR® (Azacitidine), MYLOTARG® (Gemtuzumab Ozogamicin), Nanoparticle Paclitaxel (Paclitaxel Albumin-stabilized Nanoparticle Formulation), Navelbine (Vinorelbine Tartrate), Necitumumab, Nelarabine, Neosar (Cyclophosphamide), Neratinib Maleate, Nerlynx (Neratinib Maleate), Netupitant and Palonosetron Hydrochloride, NEULASTA® (Pegfilgrastim), NEUPOGEN® (Filgrastim), Nexavar (Sorafenib Tosylate), Nilandron (Nilutamide), Nilotinib, Nilutamide, Ninlaro (Ixazomib Citrate), Niraparib Tosylate Monohydrate, Nivolumab, Nolvadex (Tamoxifen Citrate), Nplate (Romiplostim), Obinutuzumab, Odomzo (Sonidegib), OEPA (O=Vincristine Sulfate (Oncovin), E=Etoposide Phosphate, P=Prednisone, A=Doxorubicin Hydrochloride (Adriamycin)), Ofatumumab, OFF (O=Oxaliplatin, F=Fluorouracil, F=Leucovorin Calcium (Folinic Acid)), Olaparib, Olaratumab, Omacetaxine Mepesuccinate, ONCASPAR® (Pegaspargase), Ondansetron Hydrochloride, Onivyde (Irinotecan Hydrochloride Liposome), Ontak (Denileukin Diftitox), OPDIVO® (Nivolumab), OPPA (O=Vincristine Sulfate (Oncovin), P=Procarbazine Hydrochloride, P=Prednisone, A=Doxorubicin Hydrochloride (Adriamycin)), Osimertinib, Oxaliplatin, Paclitaxel, Paclitaxel Albumin-stabilized Nanoparticle Formulation, PAD (P=Bortezomib (PS-341), A=Doxorubicin Hydrochloride (Adriamycin), D=Dexamethasone), Palbociclib, Palifermin, Palonosetron Hydrochloride, Palonosetron Hydrochloride and Netupitant, Pamidronate Disodium, Panitumumab, Panobinostat, Paraplat (Carboplatin), PARAPLATIN® (Carboplatin), Pazopanib Hydrochloride, PCV, PEB, Pegaspargase, Pegfilgrastim, Peginterferon Alfa-2b, PEG-Intron (Peginterferon Alfa-2b), Pembrolizumab, Pemetrexed Disodium, Perjeta (Pertuzumab), Pertuzumab, Platinol (Cisplatin), Platinol-AQ (Cisplatin), Plerixafor, Pomalidomide, POMALYSTR (Pomalidomide), Ponatinib Hydrochloride, PORTRAZZA® (Necitumumab), Pralatrexate, Prednisone, Procarbazine Hydrochloride, Proleukin (Aldesleukin), PROLIA® (Denosumab), PROMACTA® (Eltrombopag Olamine), Propranolol Hydrochloride, PROVENGE® (Sipuleucel-T), PURINETHOL® (Mercaptopurine), PURIXAN® (Mercaptopurine), Radium 223 Dichloride, Raloxifene Hydrochloride, Ramucirumab, Rasburicase, R-CHOP (R=Rituximab and CHOP), R-CVP (R=Rituximab and CVP), Recombinant Human Papillomavirus (HPV) Bivalent Vaccine, Recombinant Human Papillomavirus (HPV) Nonavalent Vaccine, Recombinant Human Papillomavirus (HPV) Quadrivalent Vaccine, Recombinant Interferon Alfa-2b, Regorafenib, RELISTOR® (Methylnaltrexone Bromide), R-EPOCH, REVLIMID® (Lenalidomide), Rheumatrex (Methotrexate), Ribociclib, R-ICE (R=Rituximab and ICE), RITUXAN® (Rituximab), Rituxan Hycela (Rituximab and Hyaluronidase Human), Rituximab, Rituximab and Hyaluronidase Human, Rolapitant Hydrochloride, Romidepsin, Romiplostim, Rubidomycin (Daunorubicin Hydrochloride), RUBRACA® (Rucaparib Camsylate), Rucaparib Camsylate, Ruxolitinib Phosphate, RYDAPT® (Midostaurin), Sclerosol Intrapleural Aerosol (Talc), Siltuximab, Sipuleucel-T, Somatuline Depot (Lanreotide Acetate), Sonidegib, Sorafenib Tosylate, SPRYCEL® (Dasatinib), STANFORD V, Sterile Talc Powder (Talc), Steritalc (Talc), STIVARGA® (Regorafenib), Sunitinib Malate, SUTENT® (Sunitinib Malate), Sylatron (Peginterferon Alfa-2b), SYLVANT® (Siltuximab), SYNRIBO® (Omacetaxine Mepesuccinate), TABLOID® (Thioguanine), TAC (T=Docetaxel (Taxotere), A=Doxorubicin Hydrochloride (Adriamycin), C=Cyclophosphamide), Tafinlar (Dabrafenib), TAGRISSO® (Osimertinib), Talc, Talimogene Laherparepvec, Tamoxifen Citrate, Tarabine PFS (Cytarabine), TARCEVA® (Erlotinib Hydrochloride), TARGRETIN® (Bexarotene), TASIGNA® (Nilotinib), Taxol (Paclitaxel), TAXOTERE® (Docetaxel), Tecentriq (Atezolizumab), TEMODAR® (Temozolomide), Temozolomide, Temsirolimus, Thalidomide, THALOMID® (Thalidomide), Thioguanine, Thiotepa, Tisagenlecleucel, TolakTOLAK® (Fluorouracil—Topical), Topotecan Hydrochloride, Toremifene, TORISEL® (Temsirolimus), Tositumomab and IodineI 131 Tositumomab, TOTECT® (Dexrazoxane Hydrochloride), TPF (T=Docetaxel (Taxotere), P=Cisplatin (Platinol), F=Fluorouracil), Trabectedin, Trametinib, Trastuzumab, TREANDA® (Bendamustine Hydrochloride), Trifluridine and Tipiracil Hydrochloride, Trisenox (Arsenic Trioxide), TYKERB® (Lapatinib Ditosylate), UNITUXIN® (Dinutuximab), Uridine Triacetate, VAC (V=Vincristine Sulfate, A=Dactinomycin (Actinomycin-D), C=Cyclophosphamide), Valrubicin, VALSTAR® (Valrubicin), Vandetanib, VAMP (V=Vincristine Sulfate, A=Doxorubicin Hydrochloride (Adriamycin), M=Methotrexate, P=Prednisone), VARUBI® (Rolapitant Hydrochloride), VECTIBIX® (Panitumumab), VelP (Ve=Vinblastine Sulfate (Velban), I=Ifosfamide, P=Cisplatin (Platinol)), Velban (Vinblastine Sulfate), Velcade (Bortezomib), Velsar (Vinblastine Sulfate), Vemurafenib, Venclexta (Venetoclax), Venetoclax, Verzenio (Abemaciclib), Viadur (Leuprolide Acetate), VIDAZA® (Azacitidine), Vinblastine Sulfate, Vincasar PFS (Vincristine Sulfate), Vincristine Sulfate, Vincristine Sulfate Liposome, Vinorelbine Tartrate, VIP, Vismodegib, VISTOGARD® (Uridine Triacetate), Voraxaze (Glucarpidase), Vorinostat, VOTRIENT® (Pazopanib Hydrochloride), VYXEOS® (Daunorubicin Hydrochloride and Cytarabine Liposome), Wellcovorin (Leucovorin Calcium), XALKORI® (Crizotinib), XELODA® (Capecitabine), XELIRI (XEL=Capecitabine (Xeloda), IRI=Irinotecan Hydrochloride), XELOX (XEL=Capecitabine (Xeloda) and OX=Oxaliplatin), XGEVA® (Denosumab), XOFIGO® (Radium 223 Dichloride), XTANDI® (Enzalutamide), YERVOY® (Ipilimumab), YESCARTA® (Axicabtagene Ciloleucel), YONDELIS® (Trabectedin), ZALTRAP® (Ziv-Aflibercept), ZARXIO® (Filgrastim), ZEJULA® (Niraparib Tosylate Monohydrate), ZELBORAF® (Vemurafenib), ZEVALIN® (Ibritumomab Tiuxetan), ZINECARD® (Dexrazoxane Hydrochloride), Ziv-Aflibercept, ZOFRAN® (Ondansetron Hydrochloride), ZOLADEX® (Goserelin Acetate), Zoledronic Acid, ZOLINZA® (Vorinostat), ZOMETA® (Zoledronic Acid), ZYDELIG® (Idelalisib), ZYKADIA® (Ceritinib), ZYTIGA® (Abiraterone Acetate), or a combination thereof.

Suitable checkpoint inhibitors can comprise anti-PD1 antibodies (such as KEYTRUDA or pembrolizumab, OPDIVO® or nivolumab, BAVENCIO® or avelumab, IMFINZI® or durvalumab, TECENTRIQ® or atezolizumab), anti-PD-L1 antibodies, anti-CTLA-4 (cytotoxic T lymphocyte-associated antigen, also known as CD152) antibodies, anti-LAG3 (lymphocyte activation gene-3) antibodies, anti-TIM-3 (T cell immunoglobulin and mucin domain-3) antibodies, or a combination thereof.

Suitable therapeutic agents can comprise anti-CD19 antibodies, anti-CD20 antibodies such as tositumomab, cytokines, such as, interleukins, interferon α 2a (INF-α 2a), interferon α (INF-α), granulocyte colony stimulating factor (G-CSF) or Neupogen also known as Filgrastim, T cell receptor (TCR), chimeric antigen receptor or chimeric antigen T cell receptor (CAR-T), or a combination thereof.

This invention is further directed to a method for producing tumor inhibiting cells (TICs), the method comprising the steps of:

a) producing a xenograft tumor by dispersing a part of a tumor of a subject into a tumor cell suspension, optionally purifying tumor cells from the tumor cell suspension with one or more selected markers to produce purified tumor cells, and transplanting the tumor cell suspension or the purified tumor cells into a mammalian animal to form the xenograft tumor;

b) obtaining tumor infiltrating lymphocytes (TILs) from the xenograft tumor;

c) inactivating at least one genomic allele of at least one target gene of the TILs by introducing into the TILs a genomic modification component comprising a Cas9 protein and at least one sgRNA targeting said target gene of the TILs, wherein the genomic modification component is free from deoxyribonucleic acids exogenous to the TILs and free from viral nucleic acids;

wherein said target gene comprises Cbl-b, CTLA4, PD-1, LAG3, TIM3, CD73, KIR (killer inhibitory receptor), Fas, AHR (aryl hydrocarbon receptor), Smad2, Smad4, TGFBR (TGFβ receptor), ILT-3, or a combination thereof.

The TICs produced by this method of this invention can comprise Cbl-b$^{-/-}$ CD4$^+$ T cells, Cbl-b$^{-/-}$ CD8$^+$ T cells, Cbl-b-NK cells, PD-1$^{-/-}$ T cells, PD-1$^{-/-}$ NK cells, CTLA-4$^{-/-}$ T cells, CTLA4$^{-/-}$ NK cells, TIM-3$^{-/-}$ T cells, TIM-3$^{-/-}$ NK cells, KIP$^{-/-}$ T cells, KIR$^{-/-}$ NK cells, LAG3-T cells, LAG3$^{-/-}$ NK cells, CD73-cells, CD73$^{-/-}$ NK cells, Fas$^{-/-}$ T cells, Fas$^{-/-}$ NK cells, AHR$^{-/-}$ T cells, AHR$^{-/-}$ NK cells, Smad2$^{-/-}$ T cells, Smad2$^{-/-}$ NK cells, Smad4$^{-/-}$ T cells, Smad4$^{-/-}$ NK cells, TGFBR$^{-/-}$ T cells, TGFBR$^{-/-}$ NK cells, ILT-3$^{-/-}$ T cells, ILT-34$^{-/-}$ NK cells, or a combination thereof. The subject can be a human subject.

Any methods for producing xenograft tumor, purifying TILs, obtaining TILs from xenograft tumor, inactivating target gene that are disclosed above and hereafter can be suitable.

All references cited herein are incorporated by reference.

REFERENCES

1. Humphries, C. Adoptive cell therapy: Honing that killer instinct. Nature 504, S13-15 (2013).
2. Rosenberg, S. A. Cell transfer immunotherapy for metastatic solid cancer—what clinicians need to know. Nat. Rev. Clin. Oncol. 8, 577-585 (2011).
3. Houghton, A. N., Gold, J. S. & Blachere, N. E. Immunity against cancer: lessons learned from melanoma. Curr. Opin. Immunol. 13, 134-140 (2001).
4. Rosenberg, S. A. Progress in human tumour immunology and immunotherapy. Nature 411, 380-384 (2001).
5. Boon, T., Cerottini, J. C., Van den Eynde, B., van der Bruggen, P. & Van Pel, A. Tumor antigens recognized by T lymphocytes. Annu. Rev. Immunol. 12, 337-365 (1994).
6. Pardoll, D. M. Cancer vaccines. Nat. Med. 4, 525-531 (1998).
7. Rosenberg, S. A., Yang, J. C. & Restifo, N. P. Cancer immunotherapy: moving beyond current vaccines. Nat. Med. 10, 909-915 (2004).
8. Schuler, G., Schuler-Thurner, B. & Steinman, R. M. The use of dendritic cells in cancer immunotherapy. Curr. Opin. Immunol. 15, 138-147 (2003).
9. Somasundaram, R. et al. Inhibition of cytolytic T lymphocyte proliferation by autologous CD4$^+$/CD25$^+$ regulatory T cells in a colorectal carcinoma patient is mediated by transforming growth factor-beta. Cancer Res. 62, 5267-5272 (2002).
10. Townsend, S. E. & Allison, J. P. Tumor rejection after direct costimulation of CD8$^+$ T cells by B7-transfected melanoma cells. Science 259, 368-370 (1993).
11. Chen, L. et al. Tumor immunogenicity determines the effect of B7 costimulation on T cell-mediated tumor immunity. J. Exp. Med. 179, 523-532 (1994).
12. Ramarathinam, L., Castle, M., Wu, Y. & Liu, Y. T cell costimulation by B7/BB1 induces CD8 T cell-dependent tumor rejection: an important role of B7/BB1 in the induction, recruitment, and effector function of antitumor T cells. J. Exp. Med. 179, 1205-1214 (1994).
13. Robert, C. et al. Ipilimumab plus dacarbazine for previously untreated metastatic melanoma. N. Engl. J. Med. 364, 2517-2526 (2011).
14 Robert, C. et al. Anti-programmed-death-receptor-1 treatment with pembrolizumab in ipilimumab-refractory advanced melanoma: a randomised dose-comparison cohort of a phase 1 trial. Lancet Lond. Engl. 384, 1109-1117 (2014).
15. Boutros, C. et al. Safety profiles of anti-CTLA-4 and anti-PD-1 antibodies alone and in combination. Nat. Rev. Clin. Oncol. 13, 473-486 (2016).
16. Novartis CAR-T cell therapy CTL019 receives FDA Breakthrough Therapy designation for treatment of adult patients with r/r DLBCL. Novartis Available at: https://www.novartis.com/news/media-releases/novartis-car-t-cell-therapy-ctl019-receives-fda-breakthrough-therapy-designation.
17. Rao, N., Dodge, I. & Band, H. The Cbl family of ubiquitin ligases: critical negative regulators of tyrosine kinase signaling in the immune system. J. Leukoc. Biol. 71, 753-763 (2002).
18. Liu, Y.-C. & Gu, H. Cbl and Cbl-b in T-cell regulation. Trends Immunol. 23, 140-143 (2002).
19. Thien, C. B. & Langdon, W. Y. Cbl: many adaptations to regulate protein tyrosine kinases. Nat. Rev. Mol. Cell Biol. 2, 294-307 (2001).
20. Murphy, M. A. et al. Tissue hyperplasia and enhanced T-cell signalling via ZAP-70 in c-Cbl-deficient mice. Mol. Cell. Biol. 18, 4872-4882 (1998).
21. Bachmaier, K. et al. Negative regulation of lymphocyte activation and autoimmunity by the molecular adaptor Cbl-b. Nature 403, 211-216 (2000).
22. Chiang, Y. J. et al. Cbl-b regulates the CD28 dependence of T-cell activation. Nature 403, 216-220 (2000).
23. Naramura, M., Kole, H. K., Hu, R. J. & Gu, H. Altered thymic positive selection and intracellular signals in Cbl-deficient mice. Proc. Natl. Acad. Sci. U.S.A. 95, 15547-15552 (1998).
24. Naramura, M. et al. c-Cbl and Cbl-b regulate T cell responsiveness by promoting ligand-induced TCR down-modulation. Nat. Immunol. 3, 1192-1199 (2002).
25. Chiang, J. Y., Jang, I. K., Hodes, R. & Gu, H. Ablation of Cbl-b provides protection against transplanted and spontaneous tumors. J. Clin. Invest. 117, 1029-1036 (2007).
26. Gu, H., Jang, I., Columbia, U., Gu, H. & Jang, I. Agents and methods to elicit anti-tumor immune response. (2007).
27. Hinterleitner, R. et al. Adoptive Transfer of siRNA Cblb-Silenced CD8+T Lymphocytes Augments Tumor Vaccine Efficacy in a B16 Melanoma Model. PLOS ONE 7, e44295 (2012).
28. Andersen, R. S. et al. Dissection of T-cell Antigen Specificity in Human Melanoma. Cancer Res. 72, 1642-1650 (2012).
29. Dudley, M. E., Wunderlich, J. R., Shelton, T. E., Even, J. & Rosenberg, S. A. Generation of tumor-infiltrating lymphocyte cultures for use in adoptive transfer therapy for melanoma patients. J. Immunother. Hagerstown Md 1997 26, 332-342 (2003).
30. Fu, Y. et al. High frequency off-target mutagenesis induced by CRISPR-Cas nucleases in human cells. Nat. Biotechnol. 31, 822-826 (2013).
31. Pattanayak, V. et al. High-throughput profiling of off-target DNA cleavage reveals RNA-programmed Cas9 nuclease specificity. Nat. Biotechnol. 31, 839-843 (2013).
32. Hsu, P. D. et al. DNA targeting specificity of RNA-guided Cas9 nucleases. Nat. Biotechnol. 31, 827-832 (2013).
33. DeRose, Y. S. et al. Patient-derived models of human breast cancer: protocols for in vitro and in vivo applications in tumor biology and translational medicine. Curr. Protoc. Pharmacol. Chapter 14, Unit14.23 (2013).

34. Wang, X. et al. Engraftment of human central memory-derived effector CD8⁺ T cells in immunodeficient mice. Blood 117, 1888-1898 (2011).

35. Kim, S., Kim, D., Cho, S. W., Kim, J. & Kim, J.-S. Highly efficient RNA-guided genome editing in human cells via delivery of purified Cas9 ribonucleoproteins. Genome Res. 24, 1012-1019 (2014).

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

Materials and Methods

Sources of T Cells:

Human primary T cells were purified from the peripheral blood of healthy donors. Human TILs were isolated from fresh breast tumor specimens according to approved procedures and protocols.

Isolation of T Cells from Blood:

About 40 mL of venous blood was collected from each healthy donor recruited at the clinic facilities of Institut de Recherche Clinique de Montréal (IRCM) according to a protocol approved by the IRCM's ethic committee.

Peripheral blood mononuclear cells (PBMCs) were isolated by gradient density separation using the Lymphoprep medium and SepMate tubes from STEMCELL™ Technologies (Vancouver, BC, V6A 1B6, Canada) according to the manufacturer's instructions. Human primary T cells or CD8⁺ T cells were then purified from PBMCs using the EasySep™ Human T Cell Isolation Kit or EasySep CD8⁺ T Cell Isolation Kit from STEMCELL™ Technologies, according to the manufacturer's instructions.

Isolation of Tumor Infiltrating (TIL) T Cells:

Fresh breast tumor specimens were obtained from patients recruited with informed consent under local ethic committee approval according to a protocol approved by appropriated ethic committees. The specimens were processed according to a protocol adapted from approved lab procedure: briefly, tumor specimens were cut into small pieces (approximately 2-3 mm³ in size) with a scalpel. Each tumor specimen piece was placed into one well of a 48-well tissue culture plate with 0.5 mL of the complete RPMI medium (RPMI 1640, 25 mM Hepes pH7.2, 100 U/mL penicillin, 100 µg/mL streptomycin, 2 mM L-glutamine, and $5.5 \times 10^{-5}$ M β-mercaptoethanol, 10% heat-inactivated fetal calf serum), supplemented with 6000 IU/mL rhIL-2. The plates were incubated in an incubator at 37° C. with 5% $CO_2$. Tumor infiltrating T cells (also referred to as tumor infiltrating lymphocytes (TILs) were growing out of the specimen pieces as individual cells. When the culture reached 80% confluence, cells from these wells were pooled and further cultured in 6-cm tissue culture dishes at a density of $1.5 \times 10^6$ cells/mL in the complete RPMI medium in the presence of 5 µg/mL anti-CD3 antibody (clone OKT3) and 5 µg/mL anti-CD28 antibody (clone CD28.2) together with 1000 U/mL IL-15, until the culture in each dish became confluent or almost confluent, typically in 2-3 weeks. Total TILs produced from the breast cancer specimen are shown in FIG. 2A with FACS sorting, wherein T cells in the TILs were gated as indicated with the lined area and harvested. The T cells were stained with anti-CD4 and anti-CD8 antibodies and FACS sorted as shown in FIG. 2B with percentages of CD4⁺ and CD8⁺ cells indicated. DIC (Differential Interference Contrast) views are also shown: one piece of breast cancer specimen grew in a 48-well tissue culture plate (FIG. 2C) and a high magnification view of breast cancer TILs in the culture (FIG. 2D).

Design of the Cbl-b Targeting sgRNA$^{Cbl-b}$

The sgRNA$^{Cbl-b}$ targeting the Cbl-b gene was designed using in-house software. The CRISPR-Cas9 editing approach can generate off-target (OT) mutations that may create unwanted consequences such as cancers. In this regard, it is necessary to minimize this risk by choosing a proper sgRNA for Cbl-b gene mutation. OT mutations are induced when a sgRNA anneals at another place in the genome, and can happen even if the off-target sequence presents some mismatches with the original sequence, particularly in the PAM-distal region. To minimize the potential danger of OT events and to avoid the potential for generating a dominate negative Cbl-b mutation, sgRNA targeting the human Cbl-b gene was designed using in-house software that is homologous to a sequence located upstream of the RING finger domain of the Cbl-b gene. The sequence of the sgRNA used was the following:

(SEQ ID. 1)
GAGGUCCACCAGAUUAGCUCUGG.

sgRNA

A template for in vitro transcription was generated by PCR using the following primers: TTAATACGACTCAC-TATAGAGGTCCACCAGATTAGCTCGTTTTAGAGCTA GAAATAGCAA (SEQ ID. 2) and AAAAGCACCGACTCGGTGCCA (SEQ ID. 3) and a PCR template consisting of a pUC57 plasmid containing an sgRNA scaffold synthetized by Genscript® according to Church lab's published sequence (available here: https://media.addgene.org/cms/files/hCRISPR_gRNA_Synthesis-.pdf, hereby incorporated by reference). The sequence of the template in the pUC57 plasmid is the following:

(SEQ ID. 4)
TGTACAAAAAAGCAGGCTTTAAAGGAACCAATTCAGTCGACTGGATCCGG

TACCAAGGTCGGGCAGGAAGAGGGCCTATTTCCCATGATTCCTTCATATT

TGCATATACGATACAAGGCTGTTAGAGAGATAATTAGAATTAATTTGACT

GTAAACACAAAGATATTAGTACAAAATACGTGACGTAGAAAGTAATAATT

TCTTGGGTAGTTTGCAGTTTTAAAATTATGTTTTAAAATGGACTATCATA

TGCTTACCGTAACTTGAAAGTATTTCGATTTCTTGGCTTTATATATCTTG

TGGAAAGGACGAAACACCGAGTGTGGCGCGGGACTGCCGTTTTAGAGCTA

GAAATAGCAAGTTAAAATAAGGCTAGTCCGTTATCAACTTGAAAAAGTGG

CACCGAGTCGGTGCTTTTTTTCTAGACCCAGCTTCTTGTACAAAGTTGG

CATTA.

The PCR product was purified using QIAquick® PCR purification kit from Qiagen and submitted to in vitro transcription using MEGAshortscript™ T7 Transcription Kit (Thermo Fisher Scientific, Waltham, MA, USA) according to the manufacturer's instructions. The final sgRNA product, sgRNA$^{Cbl-b}$, was finally purified using RNeasy® mini kit (Qiagen, Germantown, MD, USA). As an alternative approach, a synthetic Cbl-b sgRNA from a commercial source (Synthego, Redwood City, CA, USA) was also used.

Preparation of the Recombinant Cas9 Protein

The recombinant Cas9 protein, with a nuclear localization signal on its C-terminus and a 6xHis-tag at its N-terminus, was produced using the plasmid pET28a/Cas9-Cys (Addgene Plasmid #53261). Briefly, the plasmid pET28a/Cas9-Cys was transformed into BL-21 bacteria and the expression of the recombinant Cas9 was induced by adding 1 mM IPTG to the bacteria culture and further cultured at 30° C. overnight. Bacteria were lysed in the buffer containing 20 mM Tris, 300 mM NaCl, 20 nM Imidazol, 1 mg/mL Lysozyme, and sonicated for 10 min. The bacterial lysate was then clarified by centrifugation at 3500 rpm for 30 min and the supernatant was filtered with a 0.40 μm filter. The recombinant Cas9 protein was then purified from the supernatant using a FPLC system with a HisTrap™ High Performance column (GE Healthcare) according to the manufacturer's instructions. Purified recombinant Cas9 protein was concentrated with a Vivaspin6 MWCO100 centrifugal concentrator (GE Healthcare) and stored at –80° C. in a buffer containing 300 mM NaCl, 10 mM Tris-HCl (pH7.4), 0.2 mM EDTA, 2 mM DTT, and 50% (v/v) glycerol.

Transfection of Human T Cells

The Cas9-sgRNA$^{Cbl-b}$ ribonucleoprotein complex (15 μg Cas9 protein+20 μg sgRNA$^{Col-b}$) was produced by incubating the recombinant Cas9 protein and the sgRNA$^{Col-b}$ prepared above at 37° C. for 5 minutes. About $1 \times 10^6$ to $1 \times 10^7$ human T cells were transfected with the Cas9-sgRNA$^{Cbl-b}$ ribonucleoprotein complex using Amaxa® Human T cell Nucleofector® kit (Lonza, Allendale, NJ, USA, under respective registered trademarks), according to the manufacturer's instructions for unstimulated T cells. For mock transfection, the same number of human primary T cells were electroporated with 15 μg Cas9 protein without the sgRNA$^{Cbl-b}$. After electroporation, T cells were plated in tissue-culture dishes at a density of $1.5 \times 10^6$ cells/mL in the complete RPMI medium supplemented with 100 IU/mL rhIL-2 and 5 μM AZT, and were cultured in an incubator with 5% $CO_2$ at 30° C. for 12 hr. Transfected T cells were then cultured at 37° C. for expansion as described below.

Expansion of Transfected Human T-Cells

For further expansion, $1-2 \times 10^6$ cells/mL of transfected human T cells were incubated at 37° C. with 5% $CO_2$ in tissue culture dishes in the completed RPMI medium supplemented with 5 μg/mL anti-CD3 (clone OKT3) and 5 μg/mL anti-CD28 antibody (clone CD28.2) together with 1000 U/mL IL-15. Cells were split every three days.

Characterization of Cbl-b Inactivated T Cells

Efficiency of Cbl-b Gene Targeting:

The SURVEYOR assay was used to determine the efficiency of Cbl-b gene targeted inactivation in human T cells. Briefly, genomic DNA was extracted from the cells transfected with the Cas9-sgRNA$^{Cbl-b}$ ribonucleoprotein complex. Wild type genomic DNA from human T cells with mock transfection (Cas9 protein without the sgRNA$^{Cbl-b}$) served as a control. A 400 bp DNA fragment containing the sgRNA$^{Col-b}$ targeted modification site of the Cbl-b gene was amplified by PCR. The amplified DNA fragment was denatured, renatured and treated with Surveyor Nuclease (Integrated DNA technologies) according to the manufacturer's instructions. The proportion of wild type intact and cleaved mismatched DNA fragments in each sample was quantified by running the digestion products on the Agilent 2100

Figure 3:
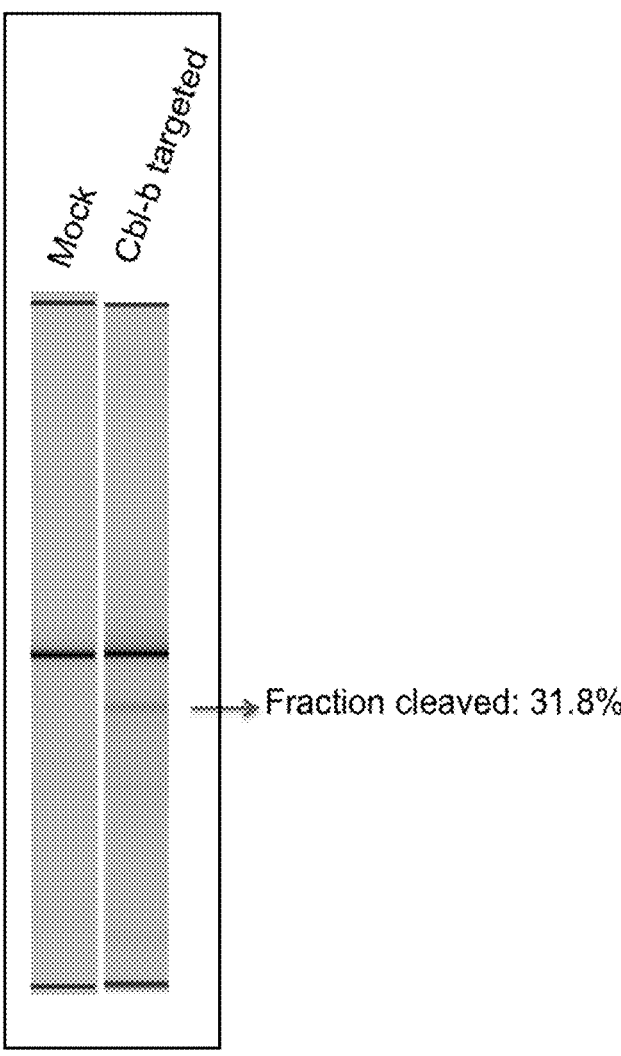
FIG. 3. A representative result of a typical Surveyor assay confirming the modification of the Cbl-b gene in primary human T cells. A 400 bp DNA fragment containing the targeting site of the Cbl-b gene was amplified by PCR, and the amplified DNA fragment was denatured, renatured, and then digested with a mismatch-specific endonuclease, Surveyor® nuclease S. The proportion of wild type intact (upper band) and cleaved mismatched (lower band) DNA fragments were calculated based on the density of each band. The percentage of the cleaved DNA indicates the proportion of the inactivated Cbl-b alleles in T cells.

Bioanalyzer (Agilent, Wilmington, DE, USA). A representative result is shown in FIG. 3.

Functional Assays:

1. T Cell Proliferative Assay

Mock-transfected or Cas9-sgRNA$^{Cbl-b}$ transfected human T cells were labeled with CFSE (Carboxyfluorescein succinimidyl ester, Life Technologies) according to the manufacturer's instructions. $2.5 \times 10^6$ CFES labeled human T cells were then cultured in 1 mL/well of the complete RPMI medium in 24-well plate with the following stimuli: 5 μg/mL plate-bound anti-human CD3 antibody (clone OKT3, Biolegend, San Diego, CA, USA) with or without 5 ng/ml recombinant human TGFβ1 (Prospec, East Brunswick NJ, USA), or 5 μg/mL plate-bound anti-human CD3 together with 2 μg/mL soluble anti-human CD28 antibody (clone CD28.2, Biolegend), with or without 5 ng/ml recombinant human TGFβ1. CFSE labeled T cells in the complete RPMI medium without CD3 or CD28 stimulations serve as a negative control. Proliferation of T cells indicated by CFSE intensity in daughter cells were measured by FACS 4 days later.

In an additional stimulation condition, we transfected the MDA-MB-231 human breast tumor cell line (ATCC #CRM-HTB-26) with human CD80 and CD83 to generate the "MDA selector" cell line and used the "MDA selector" cell line for allogeneic stimulation plus CD28 co-stimulation of human T cell cells. About $5 \times 10^5$ cells/well of irradiated "MDA selector" cells were added to $2.5 \times 10^6$ CFSE labeled mock-transfected or Cas9-sgRNA$^{Cbl-b}$ transfected human T cells in 1 mL/well of the complete RPMI medium supplemented with 200 U/mL recombinant human IL-2 in 24-well tissue culture plates. Proliferation of T cells induced by the allogeneic tumor cells were determined 7 days later with FACS to measure CFSE dilution.

2. INFγ secretion assay

Mock-transfected or Cas9-sgRNA$^{Cbl-b}$ transfected human T cells were stimulated as described above. INFγ in the culture supernatant was measured by ELISA (Affimetrix, Santa Clara, CA, USA), according to the manufacturer's instructions. INFγ secretion was also determined by an INFγ Secretion Assay-Detection Kit (Miltenyi Biotech, GmbH, Bergisch Gladbach, Germany), according to the manufacturer's instructions.

3. In Vitro Tumor Cell Killing Assay

Mock-transfected or Cas9-sgRNA$^{Cbl-b}$ transfected human T cells were labelled with CFSE and co-cultured with irradiated "MDA selector" cells described above. After 6 days of culture, T cells responding to the stimulation of "MDA selector" cells had proliferated vigorously and became CFSE$^{lo}$ cells, while the "MDA selector"-unresponsive T cells did not proliferate and remained to be CFSE$^{hi}$ cells. CFSE$^{lo}$ and CFSE$^{hi}$ cells were sorted by FACS, and were respectively cultured with "MDA selector" cells for an additional 3 days. The cytokine production (IFNγ) by T cells or viability of "MDA selector" (the target tumor cells) was analyzed by ELISA or using an LDH based cytotoxicity assay (Promega, Madison, WI, USA), respectively.

Targeted Inactivation of the Cbl-b Gene in Human Primary T Cells:

Applicant found that the mutation of the Cbl-b gene was not efficiently achieved by electroporating plasmid DNA or mRNA encoding the Cas9 protein in human primary T cells. To inactivate the Cbl-b gene in human primary T cells, recombinant Cas9 protein in complex with the in vitro transcribed sgRNA$^{Col-b}$ was used as described above. The SURVEYOR assay was used to determine the efficiency of modification of the Cbl-b gene in human T cells (FIG. 3).

Approximately 30% of the Cbl-b alleles were site-specifically inactivated in T cells isolated from the peripheral blood or from breast tumor specimens (TILs). The human T cells having the inactivated Cbl-b gene are referred to as human Cbl-b$^{-/-}$ T cells or Cbl-b$^{-/-}$ TILs, respectively.

Figure 4:
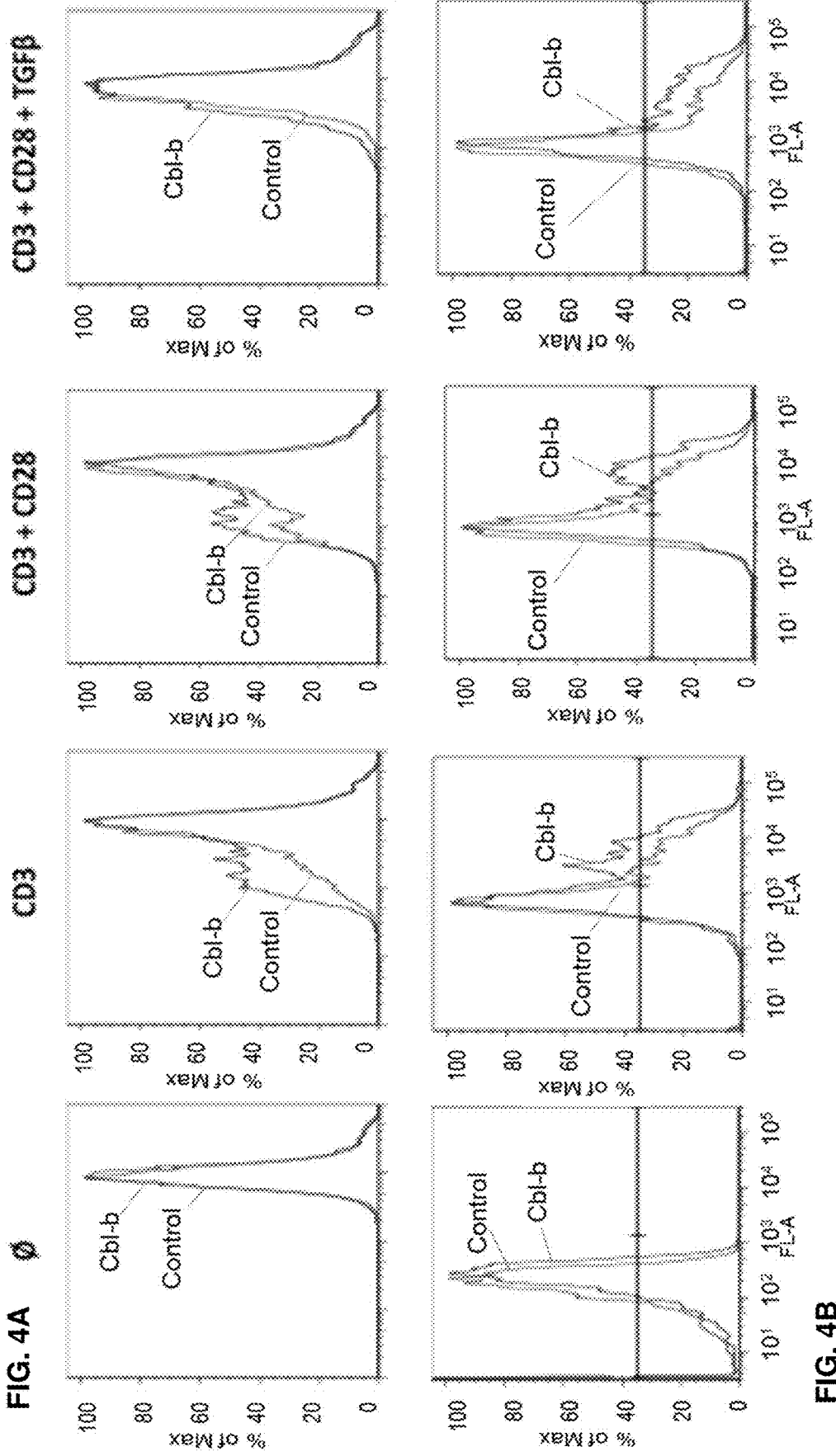
FIG. 4A-FIG. 4B. Cell function assay. (A) T cell proliferation was assessed by CFSE assay and (B) INF-γ secretion assay in response to the following stimulation conditions: Ø: no-stimulation; CD3, anti-CD3; CD3+CD28, anti-CD3+anti-CD28; CD3+CD28+TGFβ, anti-CD3+anti-CD28 and TGFβ. Control: Mock transfected cells; Cbl-b: Cas9-sgRNA$^{Cbl-b}$ transfected Cbl-b inactivated human primary Cbl-b$^{-/-}$ T cells.

Human Cbl-b$^{-/-}$ T Cells or Cbl-b$^{-/-}$ TILs are CD28 Independent for Activation And More TGFβ Resistant than Cbl-b Unmodified Human T Cells Our previous experiments showed that contrary to their wild type counterpart, mouse Cbl-b$^{-/-}$ CD8$^+$ T cells can be activated by anti-CD3 stimulation without CD28 costimulation and are resistant to TGFβ mediated suppression of cell proliferation and cytokine production. To determine whether human Cbl-b inactivated T cells (human Cbl-b$^{-/-}$ T-cells) exhibit the same functional characteristics, T cell proliferation, as well as INF-γ production, was determined after stimulation with anti-CD3 antibody, in the presence or absence of anti-CD28 and TGFβ. Cell proliferation was determined by a CFSE dilution assay (shown in FIG. 4A) and IFNγ production was measured by the IFNγ Secretion Assay kit (FIG. 4B). The human T cell population transfected with transfected with the Cas9-sgRNA$^{Col-b}$ ribonucleoprotein complex contains about 30% of human Cbl-b$^{-/-}$ T cells. As seen in mouse Cbl-b knockout T cells, human Cbl-b$^{-/-}$ T cells proliferated more vigorously and produced more IFNγ as compared to their mock transfected counterparts after stimulating with anti-CD3 alone or with anti-CD3 together with anti-CD28. Unlike the unmodified human T cells, Cbl-b$^{-/-}$ T cells were resistant to TGFβ mediated suppression.

Figure 5:
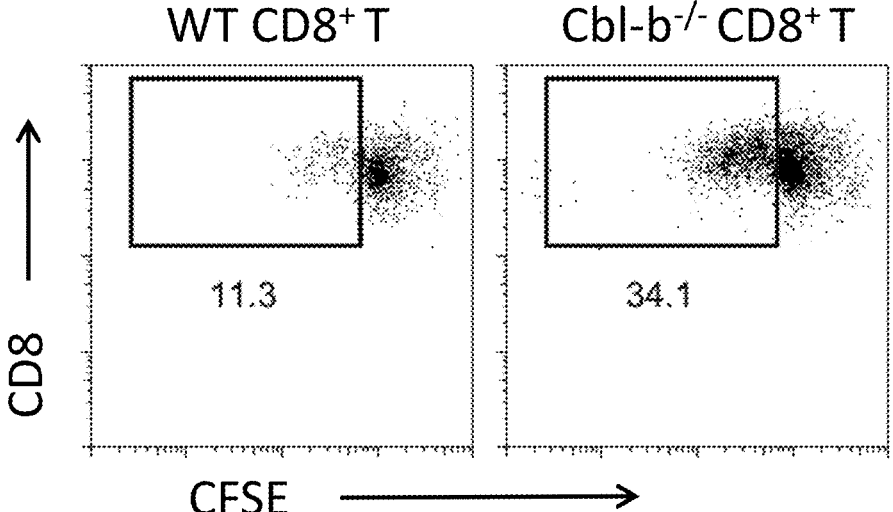
FIG. 5. TGFβ and PDL1 Inhibition Assay. Wild type control T cells (WT CD8$^+$ T) and Cbl-b$^{-/-}$ T cells (Cbl-b$^{-/-}$ CD8$^+$ T) from human breast cancer specimens were labeled with CFSE and stimulated with human breast cancer MDA-MB-231 (MDA) cells, a cell line which expresses allogenic MHC-I and high levels of PDL1 and TGFβ. After 72 hours of culture, cells were harvested, stained with anti-CD8 and analyzed on a FACS. Shown are percentages of the proliferating CD8$^+$ (CFSE$^{lo}$) T cells (rectangles within each cell type) responding to the MDA alloantigens and resistant to TGFβ and PDL1 inhibition.

Human Cbl-b$^{-/-}$ Tumor Infiltrating T Cells (Cbl-b Targeted TILs) are Resistant. To TGFβ and PDL1 Inhibition Wild type control T cells (WT CD8$^+$ T) and Cbl-b$^{-/-}$ T cells (Cbl-b$^{-/-}$ CD8+T) from human breast cancer specimens prepared above were labeled with CFSE and stimulated with human breast cancer MDA-MB-231 (MDA) cells, a cell line which expresses allogenic MHC-I and high levels of PDL1 and TGFβ. After 72 hours of culture, cells were harvested, stained with anti-CD8 and analyzed on a FACS. Shown in FIG. 5 are percentages of the proliferating CD8$^+$ (CFSE$^{lo}$) Cbl-b$^{-/-}$ CD8$^+$ T cells (rectangle, in the graph, 34.1% of total cells) responding to the MDA-MB-231 alloantigens and resistant to TGFβ and PDL1 inhibition. This is in comparison to only 11.3% of CFSE$^{lo}$ WT CD8$^+$ T cells (rectangle in corresponding graph).

Human Cbl-b$^{-/-}$ TILs Proliferate More Vigorously than Unmodified Human T Cells Upon Stimulation by a Human Tumor Cell Line Proliferation of mock-transfected (Control Cells) or Cas9-sgRNA$^{Col-b}$ transfected human TILs (Cbl-b$^{-/-}$ Cells) stimulated by the "MDA selector" cells. And labeled with CFSE. MDA selector cells were MDA-MB-231 cells transfected with human costimulatory molecules CD80 and CD83. Under this stimulation condition, human Cbl-b$^{-/-}$ TILs (Cbl-b$^{-/-}$ Cells) exhibited more cell divisions compared to their mock-transfected counterparts (Control) (FIG. 6).

Human Cbl-b$^{-/-}$ T Cells Show Increased Cytotoxicity Against a Human Tumor Cell Line than their Cbl-b Unmodified Counterpart To evaluate the anti-tumor potential of human Cbl-b$^{-/-}$ T cells, an in vitro killing assay was performed.

Human T cells from the peripheral blood were mock-transfected or transfected with the Cas9-sgRNA$^{Cbl-b}$ ribonucleoprotein complex and were labeled with CFSE. These cells were then co-cultured with the "MDA selector" tumor cells. Tumor cell-stimulated T cells proliferation resulted in the emergence of CFSE" T cells, whereas CFSE$^{hi}$ T cells were unresponsive to the "MDA selector" tumor cell stimulation.

CFSE$^{lo}$ and CFSE$^{hi}$ T cells were purified by FACS sorting. Their INFγ production (FIG. 7A) and tumor killing activity (FIG. 7B) were determined after co-cultured with the target MDA selector tumor cells. The human Cbl-b$^{-/-}$ T cells that responding to the stimulation of MDA selector (Solid circle: CFSE$^{lo}$ cells) produced more IFN-γ (FIG. 7A) and exhibited higher tumor killing activity as measured by more LDH release, relative to the mock-transfected T cells (Solid circle: CFSE$^{lo}$ cells) (FIG. 7B). The tumor-unresponsive CFSE$^{hi}$ T cells (Solid square: CFSE$^{hi}$ cells) had very low or none of tumor cells killing activities.

FIG. 7 shows: (A) ELISA measurement of INF-γ production in the supernatant of the T cell culture after stimulation by MDA-MB-231 tumor cells; (B) Tumor cell death measured by the LDH release assay. LDH release is proportional to cell death. Solid circles: CFSE$^{lo}$ cell, responders to MDA selector cells; Solid square: CFSE$^{hi}$ cells, non-responders to MDA selector tumor cells.

In Vivo Expansion of Human T Cells in Immunocompromised Mice

Figure 8:
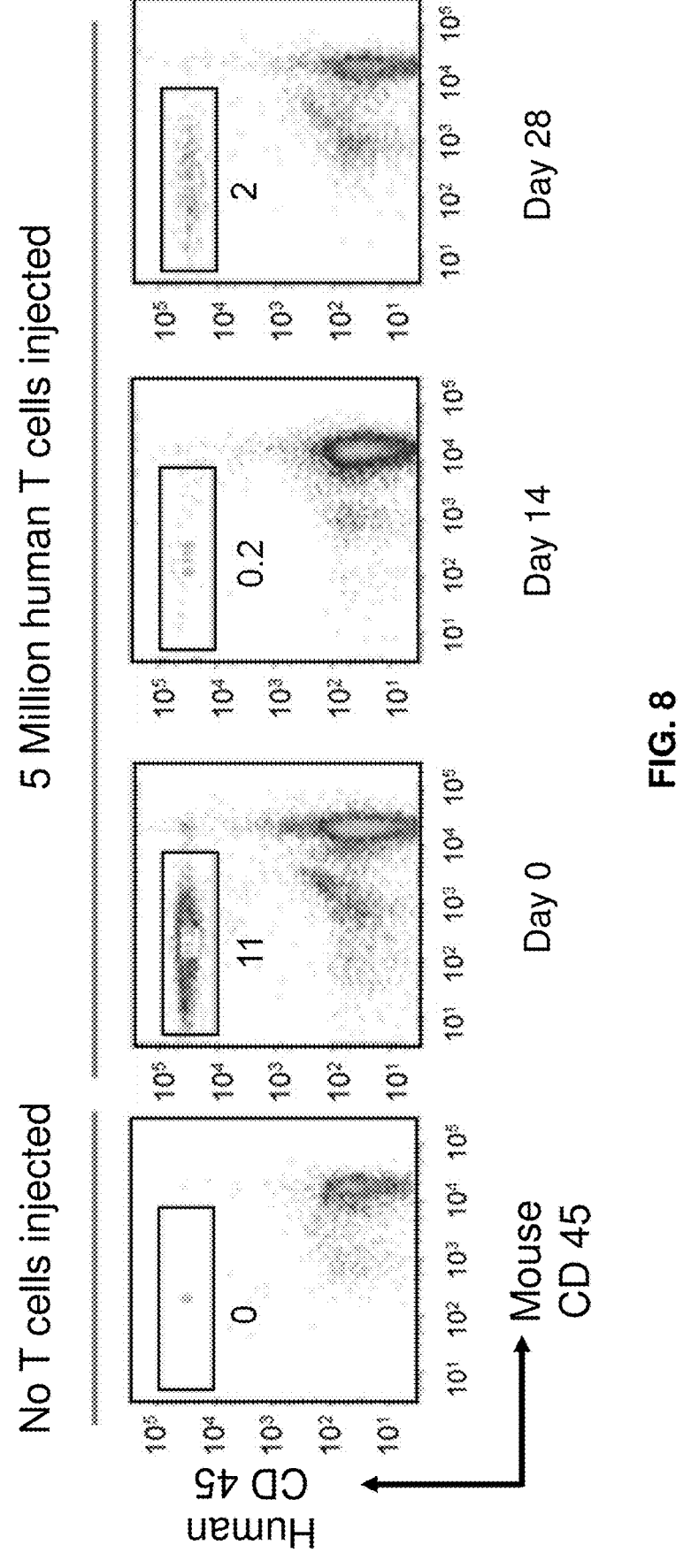
FIG. 8. Expansion and survival of human T cells after infusion into NSG mice. Purified human CD8+ T cells were transferred into NSG mice by IV injection. Shown are FACS analyses of human and mouse CD45 positive cell populations in blood circulation 28 days after IV infusion. Human T cell expansion was supported by irradiated IL-15 producing cells implanted in the same NSG mice. The population of T cells in each graph is indicated with a rectangle with percents of total cells shown.

About $10^6$ human T cells were intravenously infused into NSG mice to establish a condition that can support their engraftment and expansion by human IL-15 producing cells. Under our condition, human T cells in circulation could readily be detected 28 days after T cell-infusion (FIG. 8). This demonstrates that human T cells are able to survive and expand in vivo. This mouse system thus provides evidence that a small number of Cbl-b$^{-/-}$ T cells can expand and survive in the presence of IL-15 when administered to a human patient to induce a long-lasting anti-tumor activity.

Sequence Listing:
<210> SEQ ID. 1

<211> 23

<212> RNA

<213> Homo sapiens

<221> sgRNA

<400> 1
gagguccacc agauuagcuc ugg                                                    23

-continued

```
<210> SEQ ID. 2

<211> 60

<212> DNA

<213> Escherichia coli

<221> Primer 1

<400> 2
ttaatacgac tcactataga ggtccaccag attagctcgt tttagagcta gaaatagcaa  60

<210> SEQ ID. 3

<211> 21

<212> DNA

<213> Escherichia coli

<221> Primer 2

<400> 3
aaaagcaccg actcggtgcc a                                             21

<210> 4

<211> 455

<212> DNA

<213> Escherichia coli

<221> PUC57

<400> 4
tgtacaaaaa agcaggcttt aaaggaacca attcagtcga ctggatccgg taccaaggtc  60
gggcaggaag agggcctatt tcccatgatt ccttcatatt tgcatatacg atacaaggct 120
gttagagaga taattagaat taatttgact gtaaacacaa agatattagt acaaaatacg 180
tgacgtagaa agtaataatt tcttgggtag tttgcagttt taaaattatg ttttaaaatg 240
gactatcata tgcttaccgt aacttgaaag tatttcgatt tcttggcttt atatatcttg 300
tggaaaggac gaaacaccga gtgtggcgcg ggactgccgt tttagagcta gaaatagcaa 360
gttaaaataa ggctagtccg ttatcaactt gaaaaagtgg caccgagtcg gtgctttttt 420
tctagaccca gctttcttgt acaaagttgg catta                             455
```

---

SEQUENCE LISTING

```
Sequence total quantity: 4
SEQ ID NO: 1           moltype = RNA   length = 23
FEATURE                Location/Qualifiers
misc_feature           1..23
                       note = sgRNA
source                 1..23
                       mol_type = unassigned RNA
                       organism = Homo sapiens
SEQUENCE: 1
gaggtccacc agattagctc tgg                                           23

SEQ ID NO: 2           moltype = DNA   length = 60
FEATURE                Location/Qualifiers
misc_feature           1..60
                       note = Primer
source                 1..60
                       mol_type = other DNA
                       organism = Escherichia coli
```

-continued

```
SEQUENCE: 2
ttaatacgac tcactataga ggtccaccag attagctcgt tttagagcta gaaatagcaa   60

SEQ ID NO: 3               moltype = DNA   length = 455
FEATURE                    Location/Qualifiers
misc_feature               1..455
                           note = DNA
source                     1..455
                           mol_type = other DNA
                           organism = Escherichia coli
SEQUENCE: 3
tgtacaaaaa agcaggcttt aaaggaacca attcagtcga ctggatccgg taccaaggtc   60
gggcaggaag agggcctatt tcccatgatt ccttcatatt tgcatatacg atacaaggct  120
gttagagaga taattagaat taatttgact gtaaacacaa agatattagt acaaaatacg  180
tgacgtagaa agtaataatt tcttgggtag tttgcagttt taaaattatg tttttaaaatg  240
gactatcata tgcttaccgt aacttgaaag tatttcgatt tcttggcttt atatatcttg  300
tggaaaggac gaaacaccga gtgtggcgcg ggactgccgt tttagagcta gaaatagcaa  360
gttaaaataa ggctagtccg ttatcaactt gaaaaagtgg caccgagtcg gtgctttttt  420
tctagaccca gctttcttgt acaaagttgg catta                             455

SEQ ID NO: 4               moltype = DNA   length = 21
FEATURE                    Location/Qualifiers
misc_feature               1..21
                           note = Primer 2
source                     1..21
                           mol_type = other DNA
                           organism = Escherichia coli
SEQUENCE: 4
aaaagcaccg actcggtgcc a                                             21
```

What is claimed is:

1. A pharmaceutical composition comprising a population of tumor inhibiting cells (TICs) modified from immune cells, wherein the TICs comprise at least one inactivated genomic allele of at least one target gene and are free from bio-function of said target gene, and wherein said TICs are free from deoxyribonucleic acids exogenous to said immune cells and are free from viral nucleic acids exogenous to the immune cells;

wherein the immune cells comprise tumor infiltrating lymphocytes (TILs) from a tumor of a subject, a xenograft tumor derived from said tumor of said subject, or a combination thereof; and wherein said TILs inhibit one or more specific tumors including said tumor of said subject.

2. The pharmaceutical composition of claim 1, wherein said at least one target gene comprises Cbl-b, CTLA4, PD-1, LAG3, TIM3, CD73, KIR (killer inhibitory receptor), Fas (a member of the tumor necrosis factor (TNF)-receptor), AHR (aryl hydrocarbon receptor), Smad2, Smad4, TGFBR (TGF-beta receptor), ILT-3, or a combination thereof.

3. The pharmaceutical composition of claim 2, wherein said TICs comprise T cells, B-cells, NK cells, or a combination thereof.

4. The pharmaceutical composition of claim 3, wherein said TICs comprise Cbl-b$^{-/-}$ CD4$^+$ T cells, Cbl-b$^{-/-}$ CD8$^+$ T cells, Cbl-b$^{-/-}$ NK cells, PD-1$^{-/-}$ T cells, PD-1$^{-/-}$ NK cells, CTLA-4$^{-/-}$ T cells, CTLA4$^{-/-}$ NK cells, TIM-3$^{-/-}$ T cells, TIM-3$^{-/-}$ NK cells, KIP$^{-/-}$ T cells, KIR$^{-/-}$ NK cells, LAG3$^{-/-}$ T cells, LAG3$^{-/-}$ NK cells, CD73$^{-/-}$ T cells, CD73$^{-/-}$ NK cells, Fas$^{-/-}$ T cells, Fas$^{-/-}$ NK cells, AHR$^{-/-}$ T cells, AHR$^{-/-}$ NK cells, Smad2$^{-/-}$ T cells, Smad2$^{-/-}$ NK cells, Smad4$^{-/-}$ T cells, Smad4$^{-/-}$ NK cells, TGFBR$^{-/-}$ T cells, TGFBR$^{-/-}$ NK cells, ILT-3$^{-/-}$ T cells, ILT-3$^{-/-}$ NK cells, or a combination thereof.

5. The pharmaceutical composition of claim 1, wherein the TICs are histological compatible to said subject.

* * * * *